(12) United States Patent
Dymecki

(10) Patent No.: US 6,774,279 B2
(45) Date of Patent: Aug. 10, 2004

(54) USE OF FLP RECOMBINASE IN MICE

(75) Inventor: Susan M. Dymecki, Baltimore, MD (US)

(73) Assignee: Carnegie Institution of Washington, Washington, DC (US)

( * ) Notice: Subject to any disclaimer, the term of this patent is extended or adjusted under 35 U.S.C. 154(b) by 4 days.

(21) Appl. No.: 08/866,279

(22) Filed: May 30, 1997

(65) Prior Publication Data

US 2002/0170076 A1 Nov. 14, 2002

(51) Int. Cl.$^7$ .................. G01N 33/00; A01K 67/00; A01K 67/027; A01K 67/033

(52) U.S. Cl. .................. 800/3; 800/13; 800/14; 800/18

(58) Field of Search .................. 800/3, 13, 14, 800/18, 8, 9, 10

(56) References Cited

U.S. PATENT DOCUMENTS

| | | |
|---|---|---|
| 4,959,317 A | 9/1990 | Sauer |
| 5,434,066 A | 7/1995 | Bebee |
| 5,510,099 A | 4/1996 | Short |
| 5,527,695 A | 6/1996 | Hodges |
| 5,543,319 A | 8/1996 | Fournier |
| 5,654,182 A | 8/1997 | Wahl |

OTHER PUBLICATIONS

Wall, RJ Transgenic livestock: Progress and prospects for the future. Theriogenology 45: 57–68, 1996.*
Houdebine, LM Production of pharmaceutical proteins from transgenic animals. J. of Biotechnology 34: 269–287, 1994.*
Kappel et al. Regulating gene expression in transgenic animals. Curr. Opinion in Biotechnology 3: 548–553, 1992.*
Strojek and Wagner The use of transgenic animal techniques for livestock improvement. Genetic Engineering: Principles and Methods 10: 221–246, 1988.*
Sigmund, CD Viewpoint: Are studies in genetically altered mice out of control? Arterioscler. Thromb. Vasc. Biol, 1996.*
Marx, J. Learning how to suppress cancer. Science 261:1385–1387, Sep. 1993.*
Marshall, C.J. Oncogenes and cell proliferation: an overview. In "Oncogenes," ed. Glover et al., IRL Press, New York, pp. 1–21, 1989.*
Bieche et al. Genetic alterations in breast cancer. Genes, Chromosomes, and Cancer 14:227–251, 1995.*
Hartley et al. Nucleotide sequence of the yeast plasmid. Nature 286:860–865, Aug. 1980.*
Barigaga; Knockout Mice: Round Two; Science, vol. 265, Jul. 1, 1994, p. 26–28.
Buchholz; Different Thermostabilities of FLP an CRE Recombinases: Implications for Applied Site–Specific Recombination: Nucleic Acids Research, 1996, vol. 24, No. 21; Sep. 10, 1996; p. 4256–4262.

(List continued on next page.)

Primary Examiner—Anne-Marie Falk
(74) Attorney, Agent, or Firm—Morgan, Lewis & Bockius LLP

(57) ABSTRACT

A method is disclosed for producing site-specific recombination of DNA in a transgenic non-human mammal at chromosomal regions containing Flp-recognition sites (e.g., a DNA sequence containing an FRT site). The invention in particular discloses the use of site-specific recombinases such as Flp recombinase to accomplish in vivo recombination at engineered chromosomal FRT sites, thereby forming the basis of a genetic system to mark cell populations and lineages, as well as to activate, delete, mutate, or rearrange genes in vivo. DNA constructs are provided for the creation of Flp and FRT transfected eukaryotic cells or transgenic non-human mammals.

11 Claims, 3 Drawing Sheets

OTHER PUBLICATIONS

Buenzow; Expression of the Drosophila Gooseberry Locus Defines a Subset of Neuroblast Lineages in the Central Nervous System; Developmental Biology; vol. 170; Apr. 26, 1995; p. 338–349.

Chou; Use of a Yeast Site–Specific Recombinase to Produce Female Germline Chimeras in Drosophila; Genetics; Mar. 19, 1992; p. 643–653.

Cox; The FLP Protein of the Yeast 2–μm Plasmid: Expression of a Eukaryotic Genetic Recombination System in *Escherichia coli*; Science; Apr. 1, 1983; p. 4223–4227.

Dymecki; FLP Recombinase as a Tool for Mapping Cell Fate and Modifying Somatic Lineages in the Mouse Embryo; Mouse Molecular Genetics; 1995.

Dymecki; Tissue–Specific Deletion of DNA Sequences Using FLP Recombinase; Mouse Molecular Genetics; 1996.

Dymecki; Using FLP–Mediated Gene Deletions to Trace Cell Fate; Mouse Molecular Genetics; 1997.

Dymecki; Site–Specific Deletion of DNA Sequences in the Mouse Using FLP Recombinase; Santa Cruz; 1996.

Dymecki; A Modular Set of FLP, FRT and LACZ Fusion Vectors for Manipulating Genes by Site–Specific Recombination; Gene vol. 171; Jan. 1996; pp. 197–201.

Dymecki; FLP Recombinase Promotes Site–Specific DNA Recombination in Embryonic Stem Cells and Transgenic Mice; Proc. Natl. Sci.; vol. 93; Feb. 1996; pp. 6191–6196.

Flering; Targeted Delection of 5'HS2 of the Murine β–Globin LCR Reveals that it is not Essential for Proper Regulation . . . β–Globin Locus; Genes & Dev.; Aug. 1995; pp. 2203–2213.

Golic; The FLP Recombinase of Yeast Catalyzes Site–Specific Recombination in the Drosophila Genome; Cell; Nov. 1989; vol. 59, p. 449–509.

Golic; Sit Specific Recombination Between Homologous Chromosomes in Drosophila; Science vol. 252; p. 958–961.

Gu; Independent Control of Immunoglobulin Switch Recombination at Individual Switch Regions Evidenced Through Cre–Loxp–Mediated Gene Targeting; Cell; Jun. 1993; vol. 73; p. 1155–1164.

Gu; Deletion of a DNA Polymerase β Gene Segment in T Cell Type–Specific Gene Targeting; Science; May 1994; vol. 265; p. 103–106.

Jayaram; Two–Micrometer Circle Site–Specific Recombination: The Minimal Substrate and the Possible Role of Flanking Sequences; Proc. Natl. Acad. Sci.; Sep. 1985; vol. 82, p. 5875–5879.

Jung; Shutdown of Class Switch Recombination by Deletion of a Switch Region Control Element; Science; Feb. 1993; vol. 259, p. 984–987.

Kilby; Site–Specific Recombinases; Tools for Genome Engineering; Trends Genet; Dec. 1993; vol. 9, No. 12; p. 413–421.

Kuhn; Inducible Gene Targeting in Mice; Science; Sep. 1995; vol. 269, p. 1427–1429.

Kulpa; Mutations of the FLP Recombinase Gene that Cause a Deficiency in DNA Bending and Strand Cleavage; Journal of Biological Chemistry; Jan. 1993; vol. 268, p. 1101–1108.

Lakso; Targeted Oncogene Activation by Site–Specific Recombination in Transgenic Mice; Proc. Natl. Acad. Sci; Jul. 1992; vol. 89; 6232–6235.

Logie; Ligand–Regulated Site–Specific Recombination; Proc. Natl. Acad. Sci; Jun. 1995; vol. 92, p. 5940–5944.

Lu; Conjugative Transpositioin; TN916 Integrase Contains Two Independent DNA Binding Domains . . . Recognize Different DNA Sequences; The EMBO Journal; 1994; vol. 13; p. 1541–1548.

O'Gorman; Recombinase–Mediated Gene Activation and Site–Specific Integration in Mammalian Cells; Science; Mar. 1991; vol. 251; p. 1351–1355.

Orban; Tissue– and Site–Specific DNA Recombination in Transgenic Mice; Proc. Natl. Acad. Sci.; Aug. 1992; vol. 89, p. 6861–6865.

Panigrahl; The FLP Protein Contacts Both Major and Minor Grooves of its Recognition Target Sequence; Nucleic Acid Research; Oct. 1992; vol. 20, No. 22, p. 5927–5935.

Senecoff; DNA Recognition by the FLP Recombinase of the Yeast 2μ Plasmid a Mutational Analysis of the FLP Binding Site; J. Mol. Biol; Nov. 1987; vol. 21; p. 405–420.

Stark; Catalysis by Site–Specific Recombinases; Trends Genet; Dec. 1992; vol. 8, p. 432–439.

Struhl; Organizing Activity of Wingless Protein in Drosophila; Cell; Feb. 1993; vol. 72, p. 527–540.

Vetter; Site–Specific Recombinaton of Yeast 2–μm DNA Into Vitro; Proc. Natl. Acad. Sci.; Aug. 1993; vol. 80, p. 7284–7288.

Westeman; Reversible Immortilization of Mammalian Cells Mediated by Retroviral Transfer and Site–Specific Recombination; Proc. Natl. Acad. Sci.; Aug. 1996; vol. 93, p. 8971–8976.

Xu; Analysis of Genetic Mosaics in Developing an Adult Drosophila Tissues; Development; 1993; vol. 117; p. 1223–1237.

Wipley, et al.; Site–Specific Transgene Insertion: an Approach; Reprod. Fertil. Dev.; 1994; vol. 6; p. 585–588.

Ludwig, et al.; FLP–Mediated Site–Specific Recombination in Microinjected Murine Zygotes; Transgenic Research; 1996;vol. 5; p. 385–395.

Buchholz; Improved Properties of FLP Recombinase Evolved by Cycling Mutagenesis; Nature Biotechnology, vol. 16, Jul. 1998, p. 657–662.

Dymecki; Using FLP–Recombinase to Characterize Expansion of Wnt1–Expressing Neural Progenitors in the Mouse; Developmental Biology, vol. 201, 1998, p. 57–65.

Meyers; An Fgf8 Mutant Allegic Series Generated by CRE– and FLP–mediated Recombination; Nature Genetics, vol. 18, Feb. 1988, p. 136–141.

Minichiello; Point Mutation in trkB Causes Loss of NT4–Dependent Neurons Without Major Effects on Diverse BDNF Responses; Neuron, vol. 21, Aug. 1998, p. 335–345.

O'Gorman; Mouse Engineering, Science, vol. 277, Aug. 22, 1997, p. 1025.

Sauer; Site–Specific Recombination: Developments and Applications; Current Opinion in Biotechnology, vol. 5, 1994, p. 521–527.

Vooijs; Flp–Mediated Tissue–Specific Inactivation of the Retinoblastoma Tumor Suppressor Gene in the Mouse; Oncogene, vol. 17, 1998, p. 1–12.

Rodriguez et al., "Origin of the Precerebellar System," Neuron, vol. 27, Sep. 2000, pp. 475–486.

Rodriguez et al., "High–efficiency deleter mice show that FLPe is an alternative to Cr –loxP," Nature Gen tics, vol. 25, Jun. 2000, pp. 139–140.

Farl y et al., "Wedspread Recombinase Expr ssion Using FLPeR (Flipp r) Mice," Ge sis vol. 28, 2000, pp. 106–110.

* cited by examiner

A
pFRTZ

B
phACTB::FLP pWnt1::FLP

C

USE OF FLP RECOMBINASE IN MICE

GOVERNMENT RIGHTS

The invention described herein was made in the course of work under grant number R55-HD30830-01 and R01-HD30830 from the National Institutes of Health. The U.S. Government may retain certain rights in this invention.

BACKGROUND OF THE INVENTION

1. Field of the Invention

The present invention relates to the use of Flp recombinase to catalyze FRT site-specific DNA recombination in a transgenic non-human mammal, preferably a mouse.

2. Description of the Related Art

Site-specific recombinases are being developed as tools for genetic engineering because of their simplicity and precise activity in a variety of organisms. Two well studied recombinases are Flp and Cre. For use in vivo, a recombinase should be active in a transgenic non-human mammal. While Cre-mediated recombination has been successfully employed in trangenic mice, the utility of Flp recombinase in transgenic mice has not previously been established.

U.S. Pat. No. 4,959,317 discloses the use of the Cre-lox recombinase system in yeast and cultured mammalian cells, but not in transgenic mice. Other site-specific recombinases were not discussed.

U.S. Pat. No. 5,527,695 demonstrates the use of Flp recombinase in plants, but not in cultured mammalian cells or transgenic mice. A number of different site-specific recombinase systems are discussed; however, no guidance appears to be given for selecting among the different systems and their use in a transgenic mouse is not discussed.

Kilby et al. (1993) reviewed the demonstrated activities of different site-specific recombinases in cells and organisms. Table 1 shows that, to their knowledge, Flp recombinase activity in transgenic mice had not been accomplished.

Flp-mediated deletion was demonstrated in embryonic stem (ES) cells by Jung et al. (1993). Gu et al. (1993) compared the activity of Cre and Flp recombinases in ES cells and found "a major fraction of ES cells transiently transfected by the cre vector undergo Cre-loxP-mediated gene deletion (which is not the case in our hands if the related FLP/FRT system from yeast is used [Jung et al., 1993, and unpublished data])". Both papers were contributed by the Rajewsky group, and the same group has exclusively used the Cre-loxP system in transgenic mice to inactivate endogenous genes, instead of Flp recombinase (Gu et al., 1994; Kühn et al., 1995). Thus, prior to the present invention, it was thought that using Cre recombinase was preferred over using Flp recombinase.

In view of the above teachings of the related art, it is an unexpected finding of the present invention that Flp recombinase can function in a developing mammal to catalyze FRT site-specific recombination.

Moreover, although Cre recombinase has been successfully used to create specific deletions in the mouse genome, the general utility of Cre to catalyze recombination is currently being established. Therefore, an additional method is needed for generating site-specific genetic alterations in the following ways: (1) a site-specific recombinase demonstrating a different dose-sensitivity could be used in situations where proper regulation of the recombination event cannot be achieved using Cre and (2) two site-specific recombinases could be used in vivo to engineer simultaneous or sequential recombination reactions (e.g., independent gene activation or inactivation events).

For example, site-specific recombinases may be used to activate expression of a tracer molecule to mark cell lineages. Factors that influence the determination of these cell lineages can be identified by analyzing these marked cells in the genetic background of various mutations, including mutations generated using the second recombinase system. Additionally, having access to two recombinase systems allows for efficient use of the first recombinase to generate a mutation, and the second recombinase to remove any selectable markers used in generating that mutation which, if left in place, would confound interpretation of the study. A second recombinase system is desired which exploits the ability of Flp recombinase to catalyze FRT-specific recombination in a transgenic non-human mammal which can be used alone or to expand the uses of the CrelloxP system.

The present invention provides a transgenic non-human mammal with sufficient Flp recombinase activity to catalyze recombination between FRT sequences, a transgenic non-human mammal containing FRT target nucleic acid which serves as an efficient substrate for Flp, a process of in vivo gene manipulation using the transgenic non-human mammals, and a genetic system comprised of the Flp transgenic non-human mammal and the FRT target transgenic non-human mammal which contains at least one FRT sequence.

BRIEF SUMMARY OF THE INVENTION

An object of the invention is to provide a transgenic non-human mammal with Flp recombinase activity useful for manipulation of the genome in the intact mammal.

Yet another object of the invention is to provide a process of in vivo genetic engineering using Flp recombinase activity to catalyze FRT site-specific recombination in a non-human mammal.

A further object of the invention is to provide a genetic system of the transgenic non-human mammal with Flp recombinase activity and at least one nucleic acid which is a substrate for Flp recombinase (e.g., the nucleic acid contains a FRT sequence). The nucleic acid may also contain a transgene for insertion into the genome of a non-human mammal, or a region which directs homologous recombination into the genome of a non-human mammal.

In one embodiment of the invention, a transgenic non-human mammal is provided which contains a Flp transgene integrated in its genome. Optionally, at least one Flp-recognition sequence is also integrated in the genome of the transgenic non-human mammal. The Flp-recognition sequence comprises FRT or a derivative thereof such as, for example, SEQ ID NO:14 or SEQ ID NO:15. A transgenic non-human mammal of the invention contains sufficient Flp recombinase activity in a cell to catalyze recombination between Flp-recognition sequences of the cell, chromosomal and/or extrachromosomal. Flp recombinase activity may be regulated by a chemical (e.g., exogenously administered drug, endogenous metabolite), the mammal's developmental stage, its body temperature, or tissue type of the cell.

The substrate for Flp recombinase activity is a Flp-recognition sequence. The genome of the transgenic non-human mammal may comprise one Flp-recognition sequence, two Flp-recognition sequences, or more than two Flp-recognition sequences. A chimeric or mosaic transgenic non-human mammal may contain cells with different numbers of Flp-recognition sequences due to Flp-mediated recombination; when a Flp-recognition sequence is integrated on only one of the pair of homologous chromosomes, the genome will be hemizygous for the Flp-recognition sequence.

Recombination between two Flp-recognition sequences integrated on different chromosomes results in translocation between those chromosomes. Such translocations are a common means of creating mutations that lead to developmental abnormalities or tumorigenesis.

Recombination between two Flp-recognition sequences in direct repeat orientation may cause excision of an intervening DNA sequence (e.g., a gene). Although such events are potentially reversible because Flp-mediated recombination is conservative, loss of the excised DNA sequence during cell division or by degradation makes the mutation irreversible. A null mutation in any gene may be created in this way, and the function of the gene studied in specific cells and/or at specific developmental stages.

Recombination between two Flp-recognition sequences in inverted repeat orientation may cause inversion of an intervening sequence or gene. As in Salmonella phase variation, inversion may cause activation or inactivation of a gene. If gene activity is detectable (e.g., selectable marker, histochemical marker, reporter gene), cell lineages may be traced by identifying recombination events that mark a cell and its descendants through detection of gene activation or inactivation. Cell lineages may be traced independent of gene activity, by monitoring differences in the integration site of the Flp substrate.

Recombination between a Flp-recognition sequence integrated on a chromosome and a Flp-recognition sequence integrated on extrachromosomal genetic material may cause insertion of the genetic material into the chromosome. An insertion created in this manner would provide means for creating transgenic non-human mammals with site-specific integration of a single copy of the transgene at a site in the genome specified by the chromosomal Flp-recognition sequence. Transgene insertion at a defined site in the genome would ensure reproducibility of expression because confounding effects of variable chromatin structure would be minimized.

Preferably, the intervening sequence or genetic material contains a gene such as, for example, a developmental gene, essential gene, cytokine gene, neurotransmitter gene, neurotransmitter receptor gene, oncogene, tumor suppressor gene, selectable marker, or histochemical marker, or portion thereof. Recombination may cause activation or inactivation of a gene by juxtaposition of regulatory regions to the gene or separation of regulatory regions from the gene, respectively.

The transgenic non-human mammal of the invention may also contain a Cre recombinase transgene. A cell of the transgenic non-human mammal would contain sufficient Cre recombinase activity to catalyze recombination between Cre-recognition sequences (e.g., lox site) of the cell.

A second embodiment of the invention is a process for in vivo genetic engineering using the transgenic non-human mammal. Flp recombinase activity is induced in a cell containing at least two Flp-recognition sequences at a level sufficient to catalyze site-specific recombination in the cell. This results in recombination between Flp-recognition sequences in the cell. The cell may be of germ line or somatic origin. If recombination occurs in a germ cell or a totipotent cell, offspring may be produced with a genome altered by the recombination event. A process for studying carcinogenesis and its treatment is provided by using Flp-mediated recombination to cause activation of an oncogene or inactivation of a tumor suppressor gene. Candidate compounds or compositions may be screened in such a process to identify candidates that act to promote carcinogenesis (i.e., a cancer promoter) or inhibit carcinogenesis (i.e., a cancer inhibitor). Similarly, Flp-mediated recombination in a transgenic non-human mammal may be used in a process of activating ectopic expression of a gene during development, inactivating expression of a gene at a specific time or in a specific tissue, or identifying a cell lineage by activation or inactivation of a gene. The gene may be a developmental gene, essential gene, cytokine gene, neurotransmitter gene, neurotransmitter receptor gene, oncogene, tumor suppressor gene, selectable marker, or histochemical marker.

In a third embodiment of the invention, a genetic system comprising the transgenic non-human mammal and a purified nucleic acid containing at least one Flp-recognition sequence is provided. Preferred nucleic acids include the vectors described herein. Optionally, the genetic system may also comprise means for producing a transgenic non-human mammal which contains at least some portion of the purified nucleic acid; preferably, at least the Flp-recognition sequence is integrated into the genome of the transgenic non-human mammal.

As used herein, a transgenic non-human mammal is a non-human mammal into which genetic material has been introduced with a recombinant nucleic acid. The introduced genetic material may become integrated into the genome of the non-human mammal, preferably stably- or excisably-integrated into a chromosome of the non-human mammal, and be transmitted through the germ line to a succeeding generation. Alternatively, the genetic material may be maintained as an episome or an artificial chromosome.

Any such introduced genetic material is termed a transgene. If the transgene is unstable or is excised during cell division, the result will be a mosaic mammal comprised of at least two cell types with different genetic content but derived from the same zygote. Such an mammal may be used in cell lineage tracing; thus, a transgene flanked by FRT sites may be excised during ontogeny by the action of Flp recombinase. In contrast, a chimeric mammal comprises at least two genetically different cell types derived from different zygotes (e.g., a mammal resulting from injection of embryonal carcinoma or embryonic stem cells into a genetically different blastocyst). If the transgenic non-human mammal only contains the transgene in somatic cells, the transgene will not be passed to a succeeding generation through the germ line.

Preferably, the non-human mammal is a mammal for which methods to introduce a transgene are known in the art such as, for example, cow, goat, mouse, pig, rabbit, rat and sheep. Such methods of introducing genetic material include microinjection for the creation of transgenics from zygotes; and electroporation, biolistics, lipofection, calcium phosphate-DNA co-precipitation, DEAE-dextran, microinjection, and viral infection for the creation of transgenics from a cultured cell (e.g., pluripotent cells such as a teratocarcinoma or embryonal carcinoma, totipotent cells such as an embryonic stem cell) and subsequent transfer into an embryo.

The transgenic non-human mammal, the process, and the genetic system are particularly advantageous when separate control of more than one recombination event is desired in the mammalian genome. For example, integration of a loxP sequence-containing substrate may be followed by deletion of a selectable marker from the substrate which is mediated by Flp recombinase activity catalyzing recombination between FRT sequences flanking the selectable marker, and Cre-mediated recombination of the loxP-containing substrate. Integration of the loxP sequence containing substrate is preferably by homologous recombination, and expression of the co-integrated selectable marker enriches for this rare event; the second event occurs by Flp-mediated site-specific recombination which deletes the selectable marker to reduce competition from the regulatory regions of the selectable marker; and the third event of deleting gene sequences lying between loxP sites occurs by Cre-mediated site-specific recombination.

DESCRIPTION OF THE DRAWINGS

(FIG. 1A) Structure of the Flp-expression vector. To generate pFlp, sequences were removed from p16.43 (Fire et al., 1990) and replaced with aXbaI-SalI fragment containing the synthetic intron, Flp, and SV40 p(A) from pOG44 (O'Gorman et al., 1991). (FIG. 1B) Structure of the lacZ fusion vector placZ. (FIG. 1C) Structure of the target FRT vectors. The FRT-cassette was constructed in two steps. Double-stranded oligos (oligo pairs SD1/SD3 and SD2/SD4) were ligated and then amplified by PCR using oligo pair SD9/SD10. The 150-bp PCR product bracketed by AgeI sites was then inserted into pCR (Invitrogen) to generate pFRT$_2$. Oligos used to construct the FRT$_2$-AgeI cassette include SD1 (SEQ ID NO:1), SD2 (SEQ ID NO:2), SD3 (SEQ ID NO:3), SD4 (SEQ ID NO:4), SD9 (SEQ ID NO:5), and SD10 (SEQ ID NO:6).

Plasmid pFRT$_2$lacZ was generated by inserting the FRT$_2$-AgeI fragment from pFRT$_2$ into the unique AgeI site in placZ. This insertion disrupts the NLS::trpS::lacZ open reading frame; there are no ATG codons downstream of the AgeI site to start translation of functional βGal. Plasmid pFRT$_2$neo.lacZ contains the Nm$^R$ gene (XhoI-BamHI fragment) from pNeoβGal (O'Gorman et al., 1991) inserted between the BglII and XhoI sites of pFRT$_2$lacZ. The orientation of neo$^R$ is opposite to lacZ. Plasmid pFRT.lacZ was generated by digesting pFRT$_2$lacZ with XbaI and religating. Corresponding FRT vectors have been generated which contain a SV40 small t intron immediately 5' to the p(A) (XbaI-NotI fragment from pEµSv; Rosenbaum et al., 1989). These vectors are designated the "t" series (placZ.t, pFRT2lacZ.t, pFRT$_2$neo.lacZ.t and pFRT.lacZ.t). "FRT$_2$" defines two target sites in the same orientation; "FRT" refers to a single target site. Abbreviations used for restriction enzymes are as follows: AgeI (A); ApaI (Ap); AvrIIc (Av); BamHI (B); BglII (Bg); BssHII (Bs); BstBI (Bt); BstXI (Bx); EagI (E); EcoRI (RI); EcoRV (RV); HindIII (H); KpnI (K); NheI (Nh); NotI (N); PstI (P); SacI (Sa); SalI (S); SmaI (Sm); SnaBI (Sn); SpeI (Sp); SphI (Sh); Sse8387I (Ss); StuI (St); Tth111I(T); XbaI (X); XcaI (Xc); XhoI (Xh).

Figure 2:
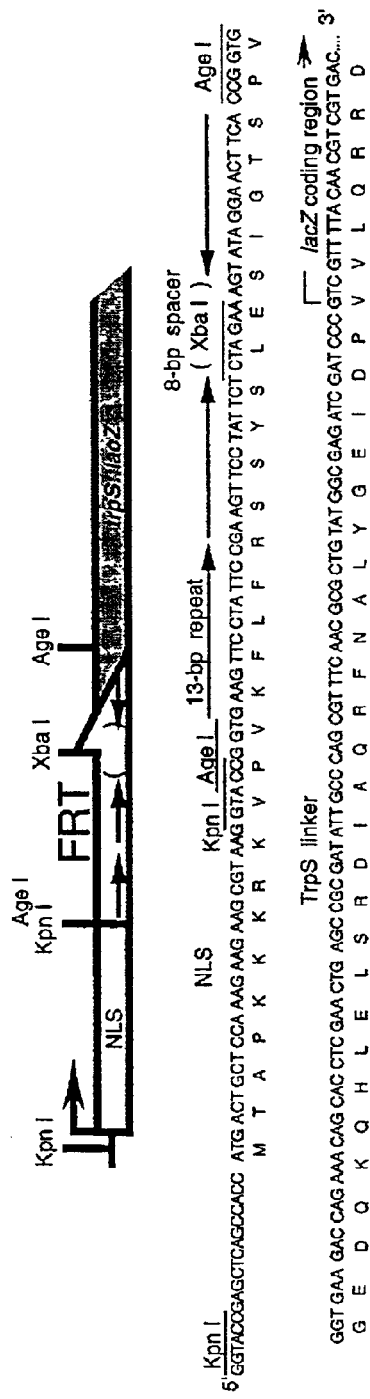

FIG. 2. Schematic and partial sequence of the βGal fusion protein predicted to be encoded by the product of Flp-mediated recombination (the nucleotide sequence shown is SEQ ID NO:7 and the protein sequence shown is SEQ ID NO:8). Linked in order are the initiating ATG codon, the 8-aa SV40 T antigen nuclear localization signal (NLS, SEQ ID NO:9), the 16-aa domain encoded by the residual FRT (SEQ ID NO:10), the 27-aa TrpS linker (SEQ ID NO:11), and βGal. The FRT consists of two 13-bp inverted repeats (SEQ ID NOS:12–13) flanking an 8-bp spacer that comprise the minimal Flp-recognition sequence (SEQ ID NO:14), plus an additional 13-bp repeat (SEQ ID NO:15).

Figure 3:
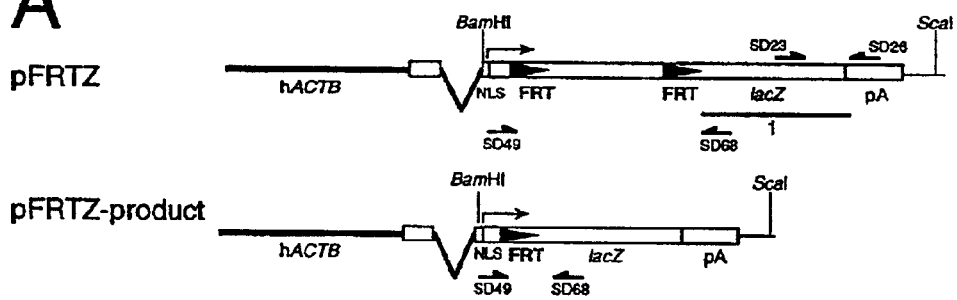
Figure 3:
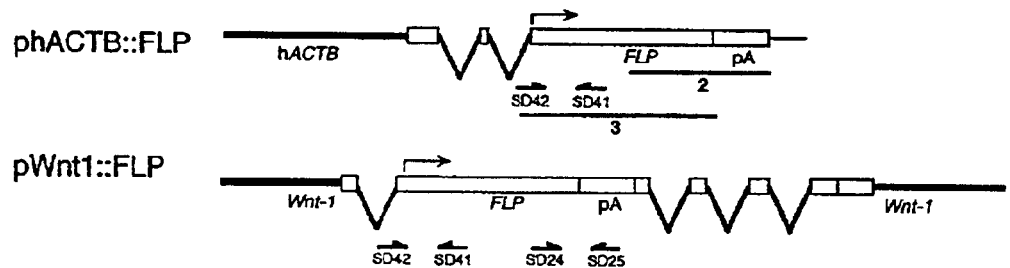
Figure 3:
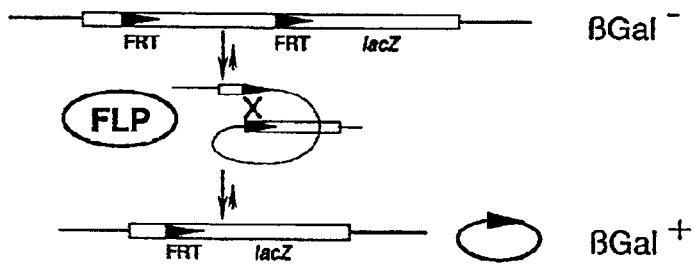

FIGS. 3A–C. DNA constructs and the Flp-mediated recombination event. Structure of target and recombinase transgenes. Flp recombination targets (FRTs) are depicted as black triangles. Rectangles represent exons; heavy lines, introns and flanking regulatory sequences; thin lines, vector sequences; and small arrows, translation start sites. Hybridization probes are represented by numbered lines. PCR oligonucleotide primers are represented by small half arrows. (FIG. 3A) Structure of target transgenes. Plasmid pFRTZ (for FRT-disrupted lacZ transgene) contains 3.9-kb of sequence from the human β-actin (hACTB) gene (Gunning et al., 1987; Zhang et al., 1994) inserted into the target vector pFRT$_2$neo.lacZ; a nuclear localization signal (NLS) and SV40 early polyadenylation (pA) sequence are also included. pFRTZ.2 is an alternative target plasmid which contains the HSV-tk gene inserted between the FRT sequences of pFRTZ. Control plasmid pFRTZ-product represents the product of Flp-mediated excisional recombination. Restriction sites and probe 1 used in Southern analyses are shown on pFRTZ. (FIG. 3B) Structure of FLP transgenes. Plasmid phACTB::FLP contains the 3.9-kb hACTB fragment inserted into the expression vector pFLP, which contains a synthetic intron, Flp-encoding sequence, and SV40 late pA sequence from pOG44 (O'Gorman et al., 1991; Stratagene). pRevhACTB::FLP contains the hACTB sequences in reverse orientation and serves as a negative control. Plasmid pWnt1::FLP contains the synthetic intron, Flp-encoding sequence and the SV40 late pA from pFLP inserted into the polylinker of the Wnt-1 expression vector pWEXP2 (26). Probe 2 is used in the whole mount in situ hybridization analyses; probe 3 is used in the Northern analyses. (FIG. 3C) Diagram of the FLP-mediated excisional recombination reaction.

DETAILED DESCRIPTION OF THE INVENTION

Site-specific recombinases of the integrase family, including Flp, are being developed as tools for genetic engineering because of their simplicity and precise activity in a broad range of organisms (Broach et al., 1982; Cox, 1983; Vetter et al., 1983; Stark et al., 1992; Kilby et al., 1993; Snaith et al., 1995). Flp recombinase from the yeast Saccharomyces cerevisiae can catalyze excision, insertion, inversion, and translocations of DNA containing Flp-recognition target sites without other cofactors (Cox, 1983; Vetter et al., 1983). The type of recombination product is determined by the orientation of target sites relative to each other on a segment of DNA (Stark et al., 1992; Kilby et al., 1993): directly repeated sites specify excision of intervening DNA, inverted sites specify inversion of intervening DNA, and sites on separate DNA molecules specify either translocation, insertion, or duplication (a special case of insertion with identical DNA molecules). Controlled recombinase expression in an organism bearing chromosomal recombinase target sites can be used to generate tissue-specific mutations, or to assess the effect of ectopic gene expression in a subset of cells with an otherwise normal organism. These applications are particularly desirable when studying the effect of lethal or otherwise deleterious mutations, or when null mutations of a gene do not result in an observable phenotype. Such controlled gene expression and manipulation can also be used to activate or inactivate a lineage tracer in populations of cells and their descendants, so that cell lineages can be identified and functionally characterized. Together, these applications provide a means to address many previously intractable problems in mammalian development.

Flp recombinase recognizes a distinct 34-bp minimal site which tolerates only limited degeneracy of its recognition sequence (Jayaram, 1985; Senecoff et al., 1988). In site-specific recombination, the substrate DNA is broken at two points and the ends are exchanged, with no synthesis or degradation of DNA (i.e., conservative recombination). For example, recombination with a circular DNA substrate can have three outcomes: a single circle resolved into two circles, two circles fused into one, or a segment within a circle can be inverted with respect to the rest of the circular molecule. To achieve a precise joint in the recombined product, the recombinase must locate the sites for cutting and rejoining the substrate, bring them together, and catalyze digestion, exchange and ligation of the substrate in a well-regulated manner. The top and bottom strand cuts are at fixed points within the crossover region but staggered, such that cleavage on both strands would give recessed 3' ends.

Controlled recombinase expression in a transgenic non-human mammal carrying appropriately placed target sites in its genome can be exploited to alter the genotype of a subset of cells within an otherwise normal embryo or adult. Such mosaic mammals bearing clones of genetically distinct somatic cells have been most extensively generated in Drosophila, providing new means to address previously intractable problems. For example, Flp-mediated excisional recombination may be used to irreversibly activate or inactivate a marker gene in specific cell populations and their descendants, allowing cell lineages to be studied; similarly, genes of interest may be ectopically expressed to study their effects on differentiation and development. By promoting mitotic exchange between target sites on homologous chromosomes, Flp provides an effective methodology for $F_1$ genetic screens. By catalyzing recombination between target sites on the same DNA molecule or between targets sites on different DNA molecules, the Flp site-specific recombinase can be used to study a variety of biological processes. Importantly, such recombination schemes can be used to generate tissue- or stage-specific mutations that would be lethal if generated in the whole organism. Controlled Flp recombinase expression, in an organism carrying chromosomal Flp recombinase target (FRT) sites, can be used to generate tissue- or stage-specific mutations, or to assess the effects of transgene expression in a subset of cells within an otherwise normal mammal.

In the examples below, the nucleotide sequence of the Flp gene used was SEQ ID NO:16 and the Flp protein had amino acid sequence SEQ ID NO:17. The wild-type Flp gene from *Saccharomyces cerevisiae* has nucleotide sequence SEQ ID NO:18 which encodes the amino acid sequence SEQ ID NO:19.

The wild-type Flp recombinase is most active at 23–30° C. and loses activity at higher temperatures. The Flp recombinase used in the examples below include the F70L mutation which has the characteristics of a temperature-sensitive mutation with activity between 23–30° C. equivalent to that of wild-type Flp recombinase, but little activity at 37° C. and above (Buchholz et al., 1996). This led to the recommendation by Stewart's group that Cre recombinase be used rather than Flp recombinase in applications that require "quantitative recombination". In contrast, the present invention illustrates the utility of non-human mammals containing Flp transgenes.

By use of the degenerate genetic code, variant nucleotide sequences may be generated that are translated into SEQ ID NO:16 and, thus, encode Flp protein. Variant nucleotide sequences may be selected for translation by considering the frequency of codon usage in the non-human mammal. Functional equivalents of the disclosed nucleotide sequence may be generated by making minor sequence variations in SEQ ID NO: 15 and measuring recombinase activity of the translated variant protein. A functional equivalent of Flp recombinase would mediate site-specific recombination more efficiently than random recombination, and produce recombined FRT sequence joints by precise cleavage and ligation. The degree of sequence variation may be assessed by low or high stringency hybridization with a target sequence of SEQ ID NO:15, or by reference to substitution of codons for chemically similar amino acid residues. Examples of Flp variants are given in Kulpa et al., (1993). Variant proteins may also be selected with desired properties such as thermolability, thermostability, altered cellular localization, altered sequence recognition, and/or modified frequency of recombination. For example, a Flp variant comprising a nuclear localization signal and Flp recombinase as a fusion protein may be used to target Flp recombinase to the nucleus, and thereby increase the frequency of recombination.

Flp recombinase activity may have its expression controlled by a regulatory region operably linked to a Flp transgene. By appropriate choice of regulatory region, Flp recombinase activity may be regulated by a chemical (e.g., drug administered to the mammal, endogenous metabolite of the mammal), developmental stage, temperature, type of tissue or cell of origin, or a combination thereof. The regulatory region may express the transgene in a broad (e.g., ubiquitously) or narrow (e.g., tissue specific) range of tissues, at varying levels of expression which may lead to different frequencies of recombination, or in a sustained or transient manner. Similar regulatory regions may be operably linked to a developmental gene, essential gene, cytoline gene, neurotransmitter, neurotransmitter receptor, oncogene, tumor suppressor gene, selectable marker, or histochemical marker to confer desired expression on the gene or marker; such gene or marker may be genetically manipulated in vivo by linkage to a Flp-recognition sequence and the action of Flp-mediated recombination.

Regulatory regions may control transcription (e.g., promoter, enhancer, silencer, rate of elongation), post-transcriptional events (e.g., editing, splicing, message stability, polyadenylation, transport out of the nucleus), translation (e.g., initiation, elongation, termination), or post-translational events (e.g., secretion and transport, cell localization, folding, assembly, protease cleavage or degradation, acylation, glycosylation, sulfation, phosphorylation, isomerization). Transcription may be regulated by, for example, tetracyline, bacteriophage RNA polymerase, IPTG, heavy metal, steroid, viral infection, expression of a DNA-binding factor, modulation of a DNA-binding factor by chemical inducers of dimerization, developmental stage, heat, tissue type, or a combination thereof. Regulatory regions may be selected from genes such as, for example, metallothionein, heat shock protein, globin, immunoglobulin heavy chain, lens crystallin, muscle creatine kinase, elastase, enolase, serum-responsive genes, major histocompatibility complex class II, interferon-responsive genes, steroid-responsive genes or the like. Regulatory regions for ubiquitous expression may be selected from genes such as, for example, β-actin, phosphoglycerate kinase, HMG-CoA reductase, major histocompatibility complex class I, β2-microglobulin, HSV thymidine kinase gene, Rous Sarcoma Virus regulatory elements, CMV immediate-early gene, SV40 origin, or the like.

Examples of regulatory regions and useful methods of gene expression are given in Goeddel (1990), Kriegler (1990), and Murray (1991). U.S. Pat. No. 5,221,778 describes a binary transgenic system comprised of a line with a transactivator-dependent promoter controlling expression of a transgene crossed to a line expressing the transactivator ubiquitously, at specific times, or in specific cells. Such a system may be used to regulate the Flp recombinase transgene in the parent or in offspring.

Examples of developmental genes that may be studied by Flp-mediated recombination include: adhesion molecules (e.g., N-CAM, cadherins, integrins), cyclin kinase inhibitors (e.g., p27, p21, p16, p15), Wnt family members, Pax family members, Winged helix family members, Hox family members, cytokines, interleukins, growth/differentiation factors (e.g., BMPs, EGF, netrin, PDGF, TGF-β) and their receptors, neurotransmitters and their receptors, kinase and phosphatases, metabolic enzymes such as tyrosine hydroxylase, antigen receptors (TCR and Ig). The gene may be expressed in a temporal and spatial pattern that mimics endogenous gene regulation to rescue lethal mutations, or otherwise complement mutant genes. While expressing the developmental gene in cells responsible for the lethal phenotype, the function of the gene may be determined in other cell types by selectively inactivating gene expression in those other cells. The function of a gene may also be determined by over expressing the gene. A developmental gene may also be expressed ectopically, that is expressed in a temporal or spatial pattern that does not mimic the endogenous patterns of expression. Thus, the function of the gene may be determined at a stage of the cell or in a type of cell with a different developmental program than is normally encountered through inactivation, over expression, or ectopic expression.

A series of recombination events may be controlled by the use of multiple Flp-recognition sites, or by the use of different site-specific recombination systems. Control of a series of recombination events may be accomplished by a competition for Flp recombinase by a multitude of identical Flp-recognition sites; recombination between identical Flp-recognition sites will then occur stochastically because the Flp-recognition sites may be used as substrates of Flp recombinase at equivalent frequencies. The physical contacts between Flp recombinase and a FRT sequence have been examined (Panigrahi et al., 1992). Alternatively, derivatives of the FRT sequence may be used as Flp-recognition sites: if the derivative is used as a substrate of Flp recombinase with lower efficiency, then Flp-mediated recombination at that site will occur less frequently; or if the derivative is used as a substrate of Flp recombinase with higher efficiency, then Flp-mediated recombination at that site will occur more frequently. Recombination between two Flp-recognition sequences results in a hybrid Flp-recognition sequence (i.e., a 13-bp repeat from a first Flp-recognition sequence and a 13-bp repeat from a second Flp-recognition sequence); thus, two barely functional FRT derivatives, each with a mutation in a 13-bp repeat (termed a half site), will exchange half sites after Flp-mediated recombination and may result in one functional FRT and one non-functional FRT. Examples of variant FRT sequences are given by Jayaram (1985) and Senecoff et al. (1988), and an assay for Flp-mediated recombination on different substrates is described by Snaith et al. (1996). Besides sequence diversity, the efficiency of Flp recombinase for a given substrate may be determined by local copy number of Flp-recognition sequences, or chromatin structure.

Recombination frequency may also be controlled by using derivatives of Flp recombinase which may have altered functions such as binding of the recognition sequence, cleavage of DNA, and rejoining of DNA. Fusion proteins comprising a Flp recombinase domain may be engineered to make recombinase activity of the fusion protein dependent on the availability of a diffusible ligand and binding of the ligand to the fusion protein (Logie and Stewart, 1995). A Flp transgene may be expressed under the control of a regulatory region that confers stage- or tissue-specific expression as described hereinabove. Flp recombinase may be expressed as part of a binary system, i.e. the Flp transgene may be operably linked to a regulatory region which is responsive to a transcription factor and the transcription factor is produced by another transgene which is integrated at a site not linked to the integration site of the Flp transgene. Preferably, the Flp transgene is regulated by a substance that is not naturally found in the transgenic host such as, for example, tetracycline (U.S. Pat. No. 5,589,362), cyclophilin (Belshaw et al., 1996), ecdysone (No et al., 1996), IPTG (U.S. Pat. Nos. 4,833,080 and 5,589,392), T7 RNA polymerase (U.S. Pat. No. 5,550,035). An alternative to controlling recombinase activity is to separate the recognition and catalytic domains of the Flp recombinase into separate polypeptides that are non-functional on their own, but that are brought together to form a functional recombinase when a diffusible binding molecule is administered to the transgenic mouse, to multimerize Flp recombinase monomers, to translocate Flp recombinase into the nucleus, or to recruit transcriptional activators that control expression of the Flp recombinase transgene (e.g., chemical inducer of dimerization; Belshaw et al., 1996; Crabtree and Schreiber, 1996); or to engineer a fusion protein of Flp and a ligand-binding domain (Logie and Stewart, 1995).

Moreover, a distinct site-specific recombination system may be used (e.g., Cre-lox) to differentially control a series of recombination events by expressing Flp and Cre recombinases independently of each other.

A genetic system with a first line of non-human mammal with a Flp transgene and a second line of transgenic non-human mammal with a transgene containing at least one Flp-recognition site is another way of regulating Flp-mediated recombination. By breeding the two transgenic lines, the Flp transgene and its substrate will be present and Flp-mediated recombination will occur in cells with sufficient Flp recombinase activity and access to substrate.

In a mosaic or a chimeric transgenic non-human mammal, cells that have undergone site-specific recombination between Flp-recognition sequences may contain different numbers of Flp-recognition sequences. In mosaic or chimeric transgenic non-human mammals that have undergone Flp-mediated inversion of a second transgene flanked by Flp-recognition sequences in inverted repeat orientation, cell lineages may be traced by activation (e.g., transcription of the sense strand by a juxtaposed regulatory region) or inactivation (e.g., deletion or separation from a regulatory region) of the second transgene. The second transgene is preferably a histochemical marker for tracing cell lineages, but in situ hybridization of transcripts from the second transgene is a possible method of detecting gene expression. Histochemical markers or reporter genes include alkaline phosphatase, β-galactosidase, choramphenicol acetyltransferase, luciferase, green fluorescent protein, β-glucoronidase, or derivatives thereof (Wasserman and DePamphilis, 1993). For in situ hybridization, radioactive labels may be used, but non-radioactive methods using an enzymatic label as described above and avidin-biotin or digoxygenin-antibody interaction. Another way of assaying gene activity would be to tag the marker gene with a peptide sequence (i.e., a fusion protein) that is capable of specific binding, and to detect the presence of the fusion protein with a cognate binder of the peptide tag. Useful peptide tag-binder pairs include, but are not limited to, avidin-biotin, GST-glutathione, polyHis-divalent metal, MBP-maltose, 9E10 Myc epitope-antibody, protein A/G-immunoglobulin, and SV40 T antigen-antibody.

Fiering et al. (1995) have described a method for gene replacement by homologous recombination, followed by site-specific recombination in ES cells to delete a selectable marker. First, the gene is replaced by homologous recombination in ES cells with positive (neo)–negative (HSV tk) selection. Homologous recombination results in retention of the neo selectable marker and loss of the HSV tk selectable marker at the homologously recombined locus, but removal of the remaining selectable marker is essential to eliminate competition between endogenous promoters and the promoter of the selectable marker. The neo expression cassette was deleted by Flp-mediated recombination in ES cells, but Fiering et al. did not express Flp recombinase in a transgenic mouse. Examples of selectable markers include neomycin phosphotransferase, hygromycin phosphotransferase, puromycin N-acetyl transferase, dihydrofolate reductase, HSV thymidine kinase, adenosine deaminase, hypoxanthine-guanine phosphoribosyl transferase, and adenine phosphoribosyl transferase. Cells carrying the marker may be selected through use of an exogenously added drug or an endogenous metabolite.

The process of screening candidate drugs that affect tumorigenesis will be directed to particular oncogenes or tumor suppressor genes. By controlling Flp-mediated recombination, such genes can be activated, inactivated, or otherwise mutated in a tissue- or temporal-specific manner. For example, MYC recombination may be directed to lymphocytes by expressing Flp recombinase with a lymphocyte-specific regulatory region from immunoglobulin heavy chain (IGH). A preferred means of activating MYC would be translocation to the IGH locus as occurs in murine plasmacytoma or human Burkitt lymphoma. A tumor suppressor gene such as RB1 could be inactivated by deletion or point mutation by expressing Flp recombinase with a crystallin regulatory region. In the foregoing, by controlling activation (MYC) or inactivation (RB1) in the cellular compartment (lymphocyte or lens, respectively) in which the gene functions, the model recapitulates a natural process of tumorigenesis.

Control of different recombination events would be useful in investigating models of multi-hit carcinogenesis, or in determining whether an immortalized or transformed phenotype can be reversed by inactivation of an oncogene (Westerman and Lebouch, 1996) or activation of a tumor suppressor gene.

A non-limiting list of oncogenes includes ABL1, BCL1, BCL2, BCL6, CBFA2, CBL, CSF1R, ERBA, ERBB, EBRB2, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3, and YES. The Flp recombinase system may be used to mutate the oncogene or its homologs by genetic means such as, for example, excision, integration (which may lead to duplication of the gene), inversion, translocation, or a combination thereof; types of mutation include amplification, deletion, gain of function, insertion, loss of expression, loss of function, over expression, or a combination thereof. Some oncogenes, especially those that encode transcription factors, are mutated by chromosome translocation or inversion; regulatory regions may be juxtaposed to the coding region of the oncogene to cause aberrant expression, or a fusion protein may be formed from all or part of the oncogene (reviewed by Rabbitts, 1994; Sorensen and Triche, 1996). Other oncogenes are often activated by point mutations that have functional consequences (e.g., gain of function, loss of function) upon translation of the oncoprotein. Oncogenes may be over expressed by gene amplification, or activation by regulatory regions that are juxtaposed by recombination next to the oncogene. Tumors may be of hematologic origin (e.g., leukemia, lymphoma) or a solid tumor.

Tumor suppressor genes include, but are not limited to, APC, BRCA1, BRCA2, MADH4, MCC, NF1, NF2, RB1, WT1, and TP53. Defined deletions of the tumor suppressor gene or its homologs may be made in whole, or in part, by Flp-mediated recombination. Flp recombinase may mutate the tumor suppressor gene or its homologs by the means previously described for oncogenes, or may induce a loss of heterozygosity by inactivating a functional tumor suppressor gene or its homologs which is allelic to a recessive mutation. The gene sequence may encode the tumor suppressor gene or its homologs, or may contain a region that regulates expression of the tumor suppressor or its homologs at the level of, for example, transcription or translation. Flp recombinase activity may induce a chromosome translocation which disrupts the coding sequence of the tumor suppressor gene or its homologs, or separates the coding sequence from essential regulatory regions. Small intragenic or large chromosome inversions may serve the same purpose.

The above-mentioned names follow the genetic nomenclature of Online Mendelian Inheritance in Man (May 1997), Center for Medical Genetics, Johns Hopkins University and National Center for Biotechnology Information, National Library of Medicine. Either the human gene or its homolog may be introduced into the non-human mammal as a transgene, or an endogenous homolog of the human gene may be genetically manipulated in the non-human mammal. Such manipulation may include introduction of one or more FRT sequences within or nearby the homologous gene by means known in the art.

All books, articles and patents cited in this specification are incorporated herein by reference in their entirety.

References

1. Belshaw, P. J., Ho, S. N., Crabtree, G. R., and Schreiber, S. L. (1996) Proc. Natl. Acad. Sci. USA 93:4604–4607.
2. Bonneret, C., Rocancourt, D., Briand, P., Grimber, G. and Nicholas, J.-F. (1987) Proc. Natl. Acad. Sci. USA 84:6795–6799.
3. Brinster, R. L., Allan, J. M., Behringer, R. R., Gelinas, R. E. and Palmiter, R. D. (1988) Proc. Natl. Acad. Sci. USA 85:836–840.
4. Broach, J. R., Guarascio, V. R. and Jayaram, M. (1982) Cell 29:227–234.
5. Buchholz, F., Ringrose, L., Angrand, P. O., Rossi, F. and Stewart, A. F. (1996) Nucleic Acids Res. 24:4256–4262.
6. Buchman, A. R. and Berg, P. (1988) Mol. Cell. Biol. 8:4395–4405.
7. Burrell, H. (1995) Epicentre Forum 2:4–5.

8. Chomczynski, P. and Sacchi, N. (1987) Anal. Biochem. 162:156–159.
9. Cox, M. M. (1983) Proc. Natl. Acad. Sci. USA 80:4223–4227.
10. Crabtree, G. R. and Schreiber, S. L. (1996) Trends Biochem. Sci. 21:418–422.
11. Echelard, Y., Epstein, D. J., St.-Jacques, B., Shen, L., Mohler, J., McMahon, J. A. and McMahon, A. P. (1993) Cell 75:1417–1430.
12. Echelard, Y., Vassileva, G. and McMahon, A. P. (1994) Development 120:2213–2224.
13. Feinberg, A. and Vogelstein, B. (1993) Anal. Biochem. 132:6–13.
14. Fire, A., Harrison, S. W. and Dixon, D. (1990) Gene 93:189–198.
15. Goeddel, D. V. (1990). *Gene Expression Technology.* Meth. Enzymol. vol. 185.
16. Gorman, C. M., Merlino, G. T., Willingham, M. C., Pastan, I. and Howard, B. H. (1982) Proc. Natl. Acad. Sci. USA 79:6777–6781.
17. Gu, H., Zou, Y.-R. and Rajewsky, K. (1993) Cell 73:1155–1164.
18. Gu, H., Marth, J. D., Orban, P. C., H. Mossmann and Rajewsky, K. (1994) Science 265:103–106.
19. Gunning, P., Leavitt, J., Muscat, G., Ng, S. and Kedes, L. (1987) Proc. Natl. Acad. Sci. USA 84:4831–4835.
20. Hall, C., Jacob, P., Ringold, G. and Lee, F. (1983) J. Mol. Appl. Genet. 2:101–109.
21. Hogan, B., Constantini, F. and Lacy, E. (1986) *Manipulating the Mouse Embryo.* CSHL Press, Plainview, N.Y., pp. 152–203.
22. Huang, M. T. F. and Gorman, C. M. (1990) Nucleic Acids Res. 18:937–947.
23. Jayaram, M. (1985) Proc. Natl. Acad. Sci. USA 82:5875–5879.
24. Jung, S., Rajewsky, K. and Radbruch, A. (1993) Science 259:984–987.
25. Kalderon, D., Richardson, W. D., Markham, A. F. and Smith, A. E. (1984a) Cell 39:499–509.
26. Kalderon, D., Richardson, W. D., Markham, A. F. and Smith, A. E. (1984b) Nature 311:33–38.
27. Kilby, N. J., Snaith, M. R. and Murray, J. A. H. (1993) Trends Genet. 9:413–421.
28. Kozak, M. (1987) Nucleic Acids Res. 15:8125–8148.
29. Kriegler, M. (1990) *Gene Transfer and Expression.* Stockton Press, New York, N.Y.
30. Kühn, R., Schwenk, F., Aguet, M. and Rajewsky, K. (1995) Science 269:1427–1429.
31. Kulpa, J., Dixon, J. E., Pan, G. and Sadowski, P. D. (1993) J. Biol. Chem. 268:1101–1108.
32. Logie, C. and Stewart, A. F. (1995) Proc. Natl. Acad. Sci. USA 92:5940–5944.
33. Murray, E. J. (1991) *Gene Transfer and Expression Protocols.* Humana Press, Clifton, N.J.
34. No, D., Yao, T. P., and Evans, R. M. (1996) Proc. Natl. Acad. Sci. USA 93:3346–3351.
35. O'Gorman, S., Fox, D. T. and Wahl, G. M. (1991) Science 251:1351–1355.
36. Panigrahi, G. B., Beatty, L. G. and Sadowski, P. D. (1992) Nucleic Acids Res. 20:5927–5935.
37. Rabbitts, T. H. (1994) Nature 372:143–149.
38. Robertson, E., Bradley, A., Kuehn, M. and Evans, M. (1986) Nature 323:445–448.
39. Robertson, E. J. (1987) In: Robertson, E. J. (Ed.), *Teratocarcinomas and Embryonic Stem Cells.* IRL Press, Oxford, pp. 71–112.
40. Rosenbaum, H., Webb, E., Adarns, J. M., Cory, S. and Harris, A. W. (1989) EMBO J. 8:749–755.
41. Rudnicki, M. A. and McBurney, M. W. (1987) In: Robertson, E. J. (Ed.) *Teratocarcinomas and Embryonic Stem Cells.* IRL Press, Oxford, pp. 19–49.
42. Sambrook, J., Fritsch, E. F. and Maniatis, T. (1989) *Molecular Cloning.* CSHL Press, Plainview, N.Y., pp. 7.43–7.52.
43. Sanes, J. R., Rubenstein, J. L. R. and Nicolas, J. F. (1986) EMBO J. 5:3133–3142.
44. Schuuring, E., Deemter, L. V., Roelink, H. and Nusse, R. (1989) Mol. Cell. Biol. 9:1357–1361.
45. Senecoff, J. F., Rossmeissl, P. J. and Cox, M. M. (1988) J. Mol. Biol. 201:405–421.
46. Snaith, M. R., Murray, J. A. H. and Boulter, C. A. (1995) Gene 166:173–174.
47. Snaith, M. R., Kilby, N. J. and Murray, J. A. (1996) Gene 180:225–227.
48. Sorensen, P. H. and Triche, T. J. (1996) Semin. Cancer Biol. 7:3–14.
49. Stark, W. M., Boocock, M. R. and Sherratt, D. J. (1992) Trends Genet. 8:432–439.
50. Stuhl, G. and Basler, K. (1993) Cell 72:527–540.
51. Thomas, K. R. and Capecchi, M. R. (1987) Cell 51:503–512.
52. Vetter, D., Andrews, B. J., Roberts-Beatty, L. and Sadowski, P. D. (1983) Proc. Natl. Acad. Sci. USA 80:7284–7288.
53. Wasserman, P. M. and DePamphilis, M. (1993) *Guide to Techniques for Mouse Development.* Meth. Enzymol. vol. 225.
54. Westerman, K. A. and Leboulch, P. (1996) Proc. Natl. Acad. Sci. USA 93:8971–8976.
55. Wilkinson, D. G., Bailes, J. A. and McMahon, A. P. (1987) Cell 50:79–88.
56. Wilkinson, D. G. (1992) In: Wilkinson, D.G. (Ed.), *In Situ Hybridization.* IRL Press, Oxford, pp. 75–83.
57. Yanisch-Perron, C., Vieira, J. and Messing, J. (1985) Gene 33:103–119.
58. Zhang, M., Kim, H., Marshall, H., Gendron-Maguire, M., Lucas, D. A., Baron, A., Gudas, L. J., Gridley, T., Krumlauf, R. and Grippo, J. F. (1994) Development 120:2431–2442.

The following examples are meant to be illustrative of the present invention; however, the practice of the invention is not limited or restricted in any way by them.

EXAMPLE 1

Flp Recombinase and Target FRT Vectors

Figure 1:
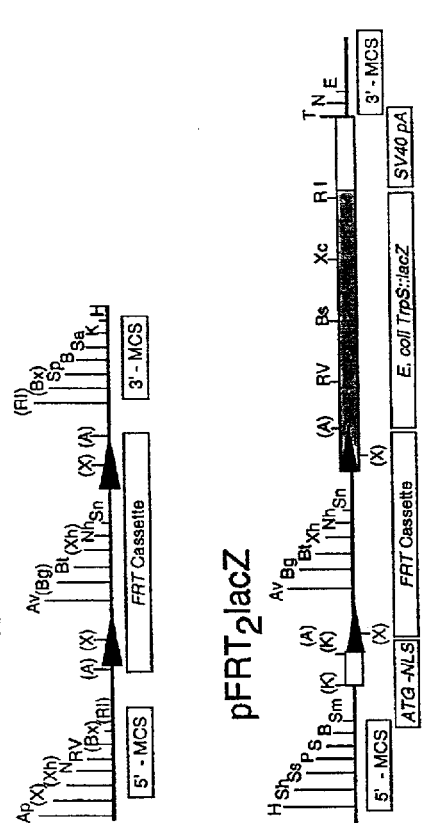
FIGS. 1A–C. Structure of the modular fusion vectors. Each functional segment is represented by a patterned rectangle (not drawn to scale); the name of each segment is boxed and described below. Enzymes in parentheses cut twice in the vectors (except plasmid pFRT$_2$ which contains three XbaI sites), all other enzymes shown are unique. A unique ClaI site at the junction of trpS and lacZ sequences is not diagrammed because it is resistant to cleavage when grown on Dam$^+$E. coli strains. All vectors, except pFRT$_2$, are built on a pUC 19-derived plasmid backbone containing Ap$^R$ (Yanisch-Perron et al., 1985; Fire et al., 1990). Plasmid pFRT$_2$ is built on a pCR backbone containing both AP$^R$ and Km$^R$ (Invitrogen). Complete sequences for all vectors are available from GenBank (accession numbers U46489-U46493).
Figure 1:
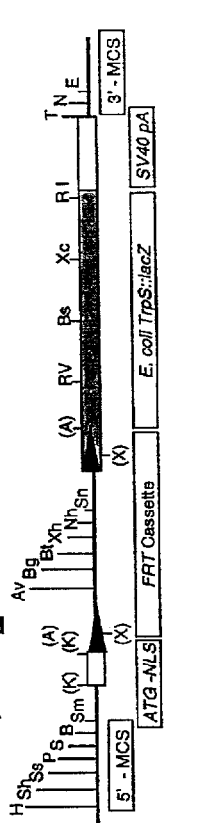
Figure 1:
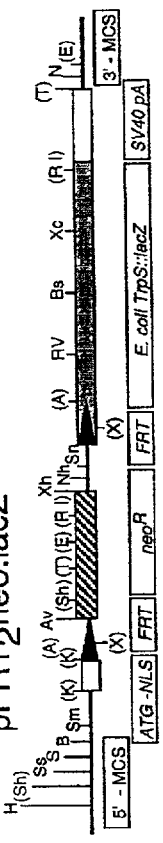
Figure 1:
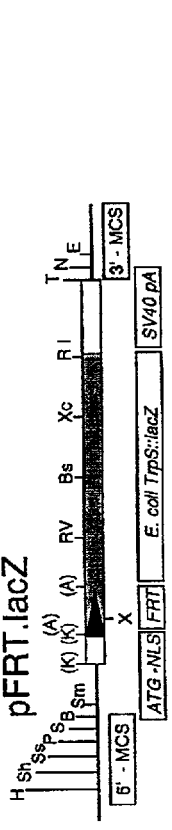
Figure 1:
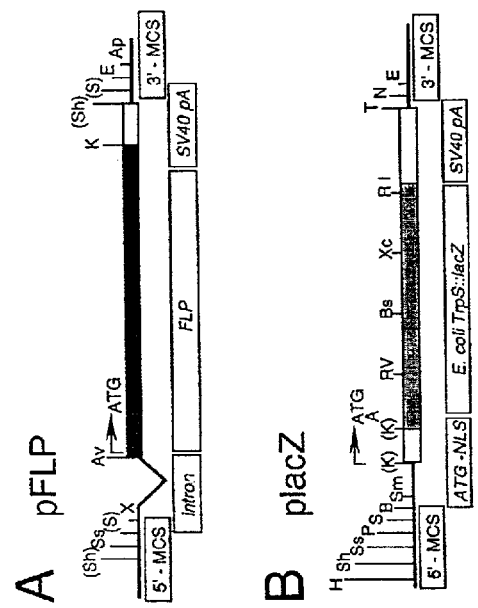
Figure 1:
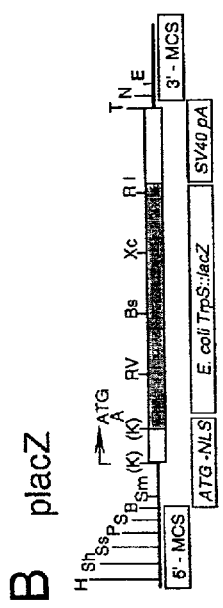

A set of versatile Flp recombinase and target vectors was constructed to facilitate using the Flp recombinase to manipulate DNA in cell culture and in the whole animal. These vectors are described below and shown in FIG. 1.

pFlp (SEQ ID NO: 15), a vector for directed expression of Flp recombinase: The pFlp plasmid contains unique 5' and 3' polylinker segments (multiple cloning sites, MCS), to facilitate insertion of regulatory elements to direct recombinase expression (FIG. 1A). This plasmid consists of a 5' MCS, Flp coding sequence (O'Gorman et al., 1991), SV40 late orientation p(A) sequence and a 3' MCS. A synthetic intron (Huang and Gorman, 1990; O'Gorman et al., 1991) has been placed upstream of the Flp coding region to maximize expression.

placZ, a lacZ fusion vector for use in vertebrate cells: Rapid and precise histochemical staining procedures make βGal a good reporter for assays of gene expression in transgenic animals. To facilitate construction of lacZ fusions for expression in vertebrate cells, the plasmid placZ has been generated. It is comprised of a 5' MCS , a KpnI-cassette containing a start Met codon and a nuclear localization signal (NLS), the βGal-coding region, SV40 early p(A) sequence and a 3' MCS (FIG. 1B).

The KpnI-cassette in placZ contains an ATG within an optimized vertebrate translation start sequence (Kozak, 1987), followed by sequences in frame that encode the NLS of SV40 T antigen (Kalderon et al., 1984a). For transcriptional fusions where translation starts at this ATG, the NLS will reside on the N-terminus of βGal and can confer tight nuclear localization upon βGal (Kalderon et al., 1984b; Bonneret et al., 1987). Nuclear-localized βGal, in contrast to cytoplasmic βGal, can help identify marked cells in the context of complex tissues and can readily be distinguished from any endogenous cytoplasmic βGal activity. Nuclear localization of βGal also permits simultaneous immunodetection of cytoplasmic cell identity markers allowing for unambiguous phenotyping of βGal marked cells. If the translation start signal and NLS are not desired, the cassette can be removed by cutting with KpnI (or Asp718I).

The βGal-coding region was derived from an *E. coli* trpS::lacZ fusion (Hall et al., 1983; Fire et al., 1990). Consequently, the lacz-containing vectors encode fusion proteins with a short peptide leader from TrpS attached to the N-terminus of βGal.

Target FRT vectors: Recombinase target vectors have been generated that allow specific combinations of FRTs, signals for RNA processing and protein targeting, selection markers, and reporter genes (or other DNA sequences) to be linked as needed (FIG. 1C).

The 'FRT$_2$-AgeI cassette' vector (pFRT$_2$) contains two recombination target sites in direct orientation flanked by AgeI sites. Each target site consists of two 13-bp inverted repeats flanking an 8-bp spacer (the minimal Flp-recognition site), plus an additional 13-bp repeat that can enhance substrate activity (Jayaram, 1985). The nucleotide sequence of a single FRTtarget site is shown in FIG. 2. In plasmid pFRT$_2$ a MCS has been engineered between the FRT sites to allow insertion of various DNA sequences.

The FRT-disrupted (silent) lacZ fusion vector, pFRT$_2$lacZ, was designed to optimize expression of lacZ and detection of βGal following Flp-mediated excisional recombination. It was generated by inserting the FRT$_2$-AgeI fragment from pFRT$_2$ into the unique AgeI site in placZ. This AgeI-insertion disrupts the NLS::trpS::lacZ open reading frame. Because there are no ATG codons to start translation of functional βGal downstream of the AgeI site, βGal activity is strictly dependent on Flp-mediated excisional recombination. Following Flp-recombination, pFRT$_2$lacZ encodes a fusion protein containing an 8-aa NLS, a 16-aa domain encoded by the residual FRT, and a 26-aa peptide leader from TrpS attached to the N-terminus of βGal (FIG. 2). This βGal fusion protein generates robust enzyme activity in mammalian cells.

Plasmid pFRT$_2$neo.lacZ contains the Nm$^R$ gene, MC1::neo$^R$::pA (O'Gorman et al., 1991), inserted between the FRTs of pFRT$_2$lacZ. The neo$^R$ gene enables selection of transgene integrants in cell culture. Plasmid pFRT.lacZ represents the expected product of Flp recombination and serves as a useful 'pre-activated' control.

To enhance transcript processing, stability and translation in mammalian cells (Brinster et al., 1988; Buchman and Berg, 1988; Huang and Gorman, 1990), a set of plasmids has been constructed that contain the SV40 small t intron immediately 5' to the p(A). The modified vectors comprise the "t" series (pFRT$_2$lacZ.t, pFRT$_2$neo.lacZ.t, pFRT.lacZ.t and placZ.t).

Considerations When Building Transcriptional Fusions

Transcriptional fusions use regulatory regions from the gene of interest linked so that translation starts at the ATG within the KpnI-NLS-cassette. When designing such fusions it is important that the initiating ATG of NLS be the first ATG codon in the mRNA. The ATG in the SphI site in the 5' MCS therefore precludes use of the HindIII and SphI sites as right-hand junctions in transcriptional fusions (Fire et al., 1990). If chosen regulatory regions contain introns, the transcriptional fusion should not be constructed in the "t" vectors. The presence of the SV40 small t intron 3' to lacZ may result in aberrant splicing if additional introns are fused 5'.

Flp-Dependent βGal Activity in Mammalian Cell Culture

The integrity of the Flp, FR T and lacZ vectors has been confirmed by restriction mapping, nucleotide sequencing and demonstration of Flp-dependent βGal activity following cotransfection of embryonic fibroblasts. For the cotransfection assays, regulatory sequences from the human β-actin-encoding gene (hACTB) were used to direct transgene expression (Gunning et al., 1987; Zhang et al., 1994). A 3.9-kb sequence from hACTB (3-kb 5' flank, 78-bp 5' untranslated region, and 832-bp first intron) was inserted into the 5' MCS sites of pFlp, pFRT$_2$neo.lacZ, pFRT.lacZ and placZ to generate phACTB::Flp, phACTB::FRT$_2$neo.lacZ, phACTB::FRT.lacZ and phACTB::lacZ, respectively.

In transient transfection experiments using primary embryonic fibroblasts (Robertson, 1987), robust nuclear βGal activity was observed by XGal histochemical staining (Sanes et al., 1986) two days following calcium phosphate transfection (Gorman et al., 1982) with the "pre-activated" constructs phACTB::FRT.lacZ and phACTB::lacZ. In contrast, βGal activity from the phACTB::FRT$_2$neo.lacZ construct was observed only following cotransfection with phACTB::Flp. Plasmid phACTB::FRT$_2$neo.lacZ transfected alone, or with Flp driven by the hACTB promoter in the reverse orientation, showed no detectable βGal activity.

Conclusions (1) Flp recombinase and FRT target vectors have been generated. When fused to hACTB regulatory sequences, these vectors have been shown to function in mammalian cells with βGal activity strictly dependent on co-expression of Flp. The SV40 NLS fused to the FRT-encoded domain (the residual FRT following recombination) can confer nuclear localization on βGal in mammalian cells. Having validated these vectors in cell culture, they are used below to establish a histochemical marking system in the mouse to study cell lineage.

(2) Because lacZ can be activated by Flp-mediated excisional recombination, these vectors would be expected to enable activation or excision of any transgene of interest.

(3) The unique restriction sites in pFlp facilitate insertion of a variety of regulatory elements to direct Flp expression, and therefore recombination, to specific cells or tissues of a transgenic non-human mammal.

(4) By coupling tissue-specific Flp expression with insertion of FRTs in the mouse genome by homologous gene replacement techniques it would be possible to delete or mutate gene segments in restricted cell populations in the transgenic non-human mammal. In this way, the effect of different mutations can be analyzed in specific cell populations in the background of an otherwise normal animal.

(5) The modularity of these vectors allows them to be readily modified for additional applications such as targeting insertions in the genome or generating chromosomal rearrangements (e.g., insertion, inversion, deletion, duplication, and translocation).

EXAMPLE 2

Materials and Methods

Plasmid Constructions and Production of Transgenic Mice

The FRT-disrupted lacZ target vector (pFRTZ; FIG. 3A) was generated by inserting the HindIII-SalI fragment from pSLhβAPr-lacZ-pA (Zhang et al., 1994) containing human β-actin (hACTB) sequences (3-kb 5' flank, 78-bp 5' untranslated region (UTR), and 832-bp first intron; Gunning et al., 1987) into the unique HindIII and SalI sites of pFRT$_2$neo.lacZ. The control plasmid pFRTZ-product was constructed by inserting the same hACTB HindIII-SalI fragment into pFRT.lacZ. A variant of pFRTZ (designated pFRTZ.2) was generated by inserting the 1.9-kb XhoI-SalI fragment from pIC19R-MC1TK (Thomas and Capecchi, 1987) containing the HSV-thymidine kinase (HSV-tk) gene between the FRT sequences of pFRTZ. Plasmid pNeoβGal (O'Gorman et al., 1991; Snaith et al., 1996; Stratagene) was also used as target DNA. The FLP transgene expression vector, phACTB::FLP (FIG. 3B), was constructed by inserting the 3.9-kb XbaI-SalI fragment from pSLhβAPr-lacZ-pA into the unique XbaI site of pFLP. A non-expressing, negative control FLP vector (pRevhACTB::FLP) was constructed which contains identical hACTB sequences in reverse orientation. To generate pWnt1::FLP, the 2-kb SalI fragment from pFLP, containing a synthetic intron, the sequence encoding Flp (O'Gorman et al., 1991; Stratagene), and SV40 early polyadenylation (pA) sequence, was inserted into the unique EcoRV site of pWEXP2 (Echelard et al., 1993). To produce transgenic mice, transgenes were purified away from plasmid sequences and injected into fertilized eggs from B6SJLF$_1$ X B6SJLF$_1$ mice as described by Hogan et al. (1986).

Cell Culture

CCE ES cells (Robertson et al., 1986) were plated onto mitomycin C-treated STO fibroblasts (Robertson, 1987) in Dulbeccos's modified Eagle medium (DMEM) supplemented with 15% fetal bovine serum (FBS), 2 mM glutamine, 0.1 mM β-mercaptoethanol, 2000 units/ml of leukemia inhibitory factor (LIF; ESGRO, Gibco BRL), 0.1 mM MEM-non essential amino acids, and 30 µM nucleosides. Primary embryonic fibroblasts (EF) were prepared from hemizygous transgenic embryos 13.5 days post coitum (dpc) as described by Robertson (1987). P19 embryonal carcinoma (EC) cells were maintained in a 1:1 mixture of DMEM and Ham F2 medium supplemented with 7.5% FBS and 2 mM glutamine.

Transient Transfection

Transient transfection of ES cells (2×10$^5$ CCE ES cells in 3.5 cm dishes) was by lipofection (Lipofectamine, Gibco BRL) using 0.5, 2 or 4 µg of plasmid phACTB::FLP (or negative control vector pRevhACTB::FLP), and 0.5 µg of either pFRTZ or pFRTZ-product. β-Galactosidase (βGal) activity was detected in situ using 4-Cl-5-Br-3-indolyl-β-d-galactosidase (XGal) (Sanes et al., 1986). Primary EF cultures were plated (5×10$^4$ cells/ml) in 3.5 cm dishes and transfected by calcium phosphate precipitation (Gorman et al., 1982) with 3 µg of the target pFRTZ or target pNeoβGal (O'Gorman et al., 1991) followed by XGal stain 48 hours later. P19 EC cells were plated (5×10$^4$ cells/ml) in 10 cm dishes. The next day, pairs of duplicate dishes were transfected by calcium phosphate precipitation (Gorman et al., 1982) with 5 µg of target pFRTZ.2 alone, 5 µg of pFRTZ.2+5 µg of phACTB::FLP, or 5 µg of pFRTZ.2+5 µg of pWnt1::FLP. Twenty-four hours later, half the dishes were treated with either 0.5 µM all-trans retinoic acid (RA, Sigma) or control diluent for an additional five days after which cells were stained with XGal.

Detection of Transcripts

Whole mount in situ hybridization to 9.5 dpc embryos was performed as described by Wilkinson (1992) using single-strand digoxigenin-UTP labeled RNA probes. The FLP probe (antisense probe 2, FIG. 3B) was a 1386-bp EcoRV-ApaI fragment from the 3' end of the FLP transgene; control probe (sense) was a 648-bp XbaI-EcoRV fragment. For Northern analyses, fresh tissue or EF cells were homogenized in 6 M guanidinium isothiocyanate and RNA isolated using acid:phenol (Chomczynski et al., 1987). Total cellular RNA (20 µg) was separated and assayed for hybridization to FLP sequence as described by Sambrook et al. (1989). Ethidium bromide staining of the gel and filter was used to confirm equivalent RNA loading.

Molecular Analysis of Transgenic Mouse Genotypes

Mouse tails were lysed with NaDodSO$_4$/proteinase K and treated with phenol/chloroform, 1:1 (vol/vol), precipitated with ethanol, and dissolved in 10 mM Tris-HCL, pH 8 and 1 mM EDTA. For PCR analysis, DNAs were amplified with the following primers: SD42 (SEQ ID NO:20) and SD41 (SEQ ID NO:21), for the FLP transgene (0.75-kb amplified fragment); SD49 (SEQ ID NO:22) and SD68 (SEQ ID NO:23), for the FRTZ transgene (1.4-kb amplified fragment) and FRTZ-product (0.25-kb fragment). The 0.25-kb PCR amplification product was cloned into plasmid pCR (Invitrogen) and sequenced; sequence analysis of the 0.25-kb product showed precise site-specific recombination. Genomic DNA isolated from freshly harvested tissues (Burrell, 1995) was subjected to BamHI/ScaI digestion, and Southern blot analyses. Radiolabeled DNA fragments (specific activity of 2–5×10$^8$ cpm/µg) for use as probes were prepared by random priming (Feinberg and Vogelstein, 1993). Transgene copy number was estimated by including standard amounts of the injected transgene in parallel. Quantitation of radioactivity in specific bands was performed with a Molecular Dynamics PhosphorImager.

Strategy Used to Assay Flp Function in Cell Culture and the Mouse

To generate a test recombination substrate for Flp function, a lacZ gene was disrupted by inserting an FRT cassette that contains stop codons in all three reading frames. This target transgene is referred to as FRTZ, for FRT-disrupted lacZ (FIG. 3A). Because the two FRT sequences flanking the cassette are in the same orientation, Flp activity should excise the intervening DNA leaving a single residual FRT in frame with lacZ (FIG. 3C). Because there are no ATG codons to initiate translation of functional βGal downstream of the FRT-cassette, βGal activity is strictly dependent on Flp-mediated excisional recombination in a manner similar to previously described gain-of-function systems (O'Gorman et al., 1991; Struhl and Basler, 1993).

To broadly express both FLP and the FRT-disrupted lacZ target (FRTZ), both transgenes were placed under the control of regulatory sequences from the human β-actin (hACTB) gene (FIG. 3A, B). These hACTB sequences have been shown to be active in most tissues in transgenic mice (Zhang et al., 1994). A "recombined" control transgene, FRTZ-product, representing the predicted product of Flp recombination was also constructed (FIG. 3A).

Flp-Mediates Efficient Recombination of Extrachromosomal DNA in ES Cells

The efficacy of Flp-mediated excisional recombination of extrachromosomal DNA in ES cells was tested by assaying for gain of βGal activity following transient cotransfection with target and recombinase plasmids. Cells were transiently transfected with either pFRTZ plus phACTB::FLP, or pFRTZ plus the negative control plasmid pRevhACTB::FLP, followed by XGal stain 48 hours later. Positive control cultures were transfected with the "recombined" plasmid, pFRTZ-product. Cultures transfected with target plasmid pFRTZ, alone or with pRevhACTB::FLP, showed no detectable βGal activity; in contrast, robust activity was observed following cotransfection with phACTB::FLP.

To estimate recombinase activity, XGal-positive cells in each transfection were counted and compared. The number of cells staining blue after transfection with the control "recombined" pFRTZ-product reflected transfection efficiency and, since constitutively active, the maximal number of βGal-positive cells. Cotransfection with a fixed amount of target plasmid and increasing amounts of FLP expression vector resulted in an increasing percentage of XGal-positive cells relative to control pFRTZ-product transfections. A comparison between experimental (pFRTZ+phACTB::FLP) and control (pFRTZ-product) transfections showed that Flp-mediated βGal activation occurred in at least 30% of transfected ES cells and could be as high as 78%. This increase in recombination with increasing Flp-encoding plasmid likely reflects more Flp protein produced per cell, as well as an increase in the proportion of cells that took up both the target and Flp-encoding plasmids (and thereby had the potential to activate lacZ).

Flp Can Be Generally Expressed in the Mouse Without Deleterious Effects

To determine whether Flp can function in the mouse and whether Flp expression, itself, would have any adverse effects, mice carrying the hACTB::FLP transgene were generated. To identify mouse lines producing Flp in a wide range of tissues, F1 mice from each founder (4917, 4924, 4925, 4927, 4921) were screened for ubiquitous FLP mRNA and recombinase activity. The distribution and amount of FLP mRNA was assessed in the embryo by whole mount in situ hybridization using antisense probe 2 (FIG. 3B) and a control sense probe, and in adult tissues by Northern analysis using hybridization to $^{32}$P-labeled probe 3 (FIG. 3B). Two of the five hACTB::FLP mouse lines exhibited broad patterns of FLP transcripts in 9.5 dpc hemizygous embryos (mouse lines 4917 and 4924) and in adult tissues (e.g., testes, brain, heart, intestine, kidney, lung, ovary, striated muscle). Line 4924 expressed in the liver, but liver expression for line 4917 was weak; line 4917 expressed in the spleen and uterus, but there was only variable expression in those organs for line 4924.

Flp recombinase activity was assayed in embryonic fibroblast (EF) cultures derived from each transgenic mouse line. Primary EF cultures were prepared from hemizygous hACTB::FLP transgenic embryos as described by Robertson (1987), transiently transfected with 3 µg of target pNEOβ-GAL plasmid (O'Gorman et al., 1991), and followed 48 hours later by histochemical Xgal staining (Sanes et al., 1986). As indicated by the number of blue cells, maximal Flp activity (approximately 45% of the "recombined" control) was observed in lines 4917 and 4924, the same mouse lines that showed broad FLP expression. The amount of recombinase activity detected in EF cultures also correlated with the amount of FLP mRNA isolated from each culture. From these results, it can be inferred that mouse lines 4917 and 4924 are the best candidates for broadly expressed active recombinase. Because no abnormalities were detected in founders or offspring, it is likely that Flp activity is nontoxic and can be used in most cell types.

Flp is Necessary and Sufficient to Recombine Target Sequences in Transgenic Mice To test whether Flp activity can recombine a chromosomal target in vivo, mice carrying the FRT-disrupted lacZtransgene, FRTZ, were generated. Five transgenic founders were obtained. $F_1$ mice from four of the five founders bred as expected for unique single-site integration events (one founder failed to transmit the transgene). Southern analysis of liver DNA isolated from each mouse line showed that three of the four mouse lines carried the target FRT-disrupted lacZ transgene in head-to-tail array: line 4999 carried an array of approximately 4 copies of the FRTZ transgene, line 4998 had 11 copies, and line 5000 had 30 copies. Transgene transmission was mendelian and no rearrangements were observed.

The ability of Flp to catalyze in vivo recombination of the target FRTZ transgene was initially examined by crossing these mouse lines with the Flp producing lines described above (4917 and 4924). Tail DNA from doubly transgenic animals was analyzed by PCR using primers (diagrammed in FIG. 3A,B) specific for detecting either the FRTZ transgene, the recombined target FRTZ-product, or the FLP transgene. Analyses of progeny from three distinct crosses are show the product of Flp-mediated excisional recombination at the FRTZ locus was amplified only in DNA isolated from doubly transgenic mice and was not detected in littermates transgenic for only the recombinase or the target gene. All three FRTZ target lines were found to be competent for recombination by this assay. Sequence analysis of the 0.25-kb amplification product showed precise site-specific recombination.

Flp Mediates Recombination in a Variety of Tissues in a Dose-Dependent Manner

The efficiency of Flp recombination at target FRTZ loci was assayed by Southern analysis. Genomic DNA isolated from doubly transgenic adult mice (target line FRTZ- 4999; FLP-4917) was hybridized with a lacZ probe (probe 1 in FIG. 3A) to allow simultaneous detection of the target FRTZ transgene and the product of recombination. The new 4.4-kb DNA fragment resulting from the recombined target was present only in samples from doubly transgenic animals, and absent in DNA isolated from either target FRTZ or FLP littermates.

The amount of recombination product detected by Southern analysis was found to correlate directly with the amount of FLP mRNA detected in each tissue by Northern hybridization examined (e.g., liver, muscle, testes). Estimates of recombination efficiency were obtained from phosphorimage quantification of recombined (4.4-kb) to non-recombined (5.6-kb) bands. In muscle, approximately 30% of the transgenes were in the recombined (4.4-kb) configuration. This represents an average of the actual recombination achieved in the various cell types isolated when dissecting muscle tissue (myofibrils, connective tissue fibroblasts, vascular endothelial cells, lymph node cells, blood cells). The value of 30% therefore represents a low estimate of the maximal recombination efficiency. This frequency is consistent with that observed in the EF cell culture assay derived from the same FLP-4917 mouse line (45%); indeed, both cell populations showed similar amounts of FLP mRNA. Hybridizing with a probe specific to DNA between the FRT sites detected only the unrecombined fragment.

The Recombined Transgene is Stably Transmitted Through the Germline

A prerequisite to using Flp to genetically manipulate cell lineages is that the recombination product be stable and heritable. Germline transmission of the recombined transgene was demonstrated by outcrossing a doubly transgenic (FRTZ-5000; FLP-4917) male and genotyping progeny by PCR. Both recombined and unrecombined transgenes were detected in this singly transgenic $F_3$ mouse indicating that recombination was incomplete; a subset of the 30 FRTZ transgenes in tandem array underwent recombination.

Conditional Expression of Flp Can Induce Regulated Rearrangement of Target Sequences in Differentiating EC Cells Controlling expression of the FLP transgene is a way to restrict recombination, and therefore gene activation or inactivation, to a specific cell population (e.g., those cells expressing sufficient Flp activity to catalyze FRT site-specific recombination). Whether Flp-mediated recombination could be induced in a differentiating EC cell culture system by using Wnt-1 regulatory sequences (Echelard et al., 1994) to express FLP (see FIG. 3B for Wnt1::FLP transgene) was investigated. Retinoic acid (RA) can induce pluripotent P19 EC cells to differentiate into a mixed population of fibroblasts, astrocytes, and neural cells (Rudnicki and McBurney, 1987; Schuuring et al., 1989). In this manner, Wnt-1 expression is likely induced specifically in neural derivatives, paralleling that seen in embryos where Wnt-1 mRNA is detected in differentiating neuroectoderm (Wilkinson et al., 1987).

P19 cells were transiently transfected with target plasmid, target plus phACTB::FLP, or target plus pWnt1::FLP; 0.5 μM RA or control diluent was added to the monolayer twenty four hours later. Following five days of RA treatment, βGal activity was assessed by histochemical XGal staining. Neural induction was monitored by morphology (the presence of long cellular processes) and culture senescence, as well as by induction of endogenous Wnt-1 mRNA.

βGal activity was detected in target plus pWnt1::FLP cotransfections only following RA induced differentiation. Similarly, endogenous Wnt-1 expression was absolutely dependent on RA. Low levels of Wnt-1 transcripts were first detected by Northern hybridization after four days of RA treatment; no Wnt-1 RNA was detected in untreated cells. As predicted by the nature of the hACTB regulatory sequences, βGal-positive cells were observed in the target plus phACTB::FLP cotransfections independent of RA. The target plasmid alone showed no activity. In addition to demonstrating regulated rearrangement of target sequences, these results define a temporal relationship between FLP expression and completed recombination. βGal activity, reflecting Flp-recombination, was observed in the target plus pWnt1::FLP cotransfection within 24 hours of first detecting Wnt-1 transcripts, and by inference Wnt1::FLP mRNA.

Conclusions

The present example demonstrates that Flp can effectively recombine extrachromsomal target DNA in ES cells, EC cells and chromosomal target DNA in transgenic mice. Flp can direct site-specific and heritable DNA recombination in the mouse, and regulated (inducible) recombination in differentiating EC cells. These properties indicate that Flp can be used to make directed modifications of a transgenic non-human mammalian genome.

Using the Flp-FRT system, recombination of an extrachromosomal target can occur in ES cells with an efficiency similar to that previously observed in mouse embryonal carcinoma (F9) cells (O'Gorman et al., 1991) and in monkey (CV-1) and human (293) embryonic kidney cells (O'Gorman et al., 1991; Logie and Stewart, 1994). Because the efficiency of Flp recombination on an extrachromosomal substrate estimated here (30–78%) is comparable to that reported for Cre on a chromosomal substrate (40–80%; Gu et al., 1993), the Flp-FRT system can likely be exploited to similarly manipulate ES cell chromosomal DNA. Towards this end, a more elaborate two-step selection scheme was employed where Flp-mediated deletion of an integrated selectable marker gene (PGK-neo) was reported to occur in 90% of Flp-expressing ES cells (Fiering et al., 1995).

In the mouse, the present example shows Flp expression is necessary and sufficient for excisional recombination of FRT target sequences. Because recombination was detected at all three chromosomal sites assayed, it is likely that most chromosomal transgenes will be accessible to Flp function. The extent of recombination observed in a given tissue correlated directly with the overall amount of FLP mRNA detected in that tissue; it is important to note that this type of tissue analysis presents an average and therefore may underestimate the maximal recombination achieved in a specific cell type. Nonetheless, these results define a dose-effect relationship which suggests that different degrees of recombination (frequent or rare) can be attained by varying the strength and specificity of the sequences used to express FLP. For some experiments, complete (quantitative) recombination may be needed. The results presented here suggest that one means to achieve this is to increase the level of FLP expression. Alternative strategies include identifying Flp variants with higher activity in mammalian cells, or to enhance the nuclear localization of Flp.

The finding that Flp can be generally expressed in the mouse without adverse effects suggests that Flp-recombination between random sequences in the mouse genome is rare. If high levels of illegitimate (non-FRT) recombination were occuring due to Flp expression, abnormalities would be expected in FLP founders or offspring. No adverse effects were detected. This result suggests that Flp can be used to mediate recombination in a variety of cell types.

Flp-mediated excisional recombination is sufficiently dose sensitive that recombination can be regulated in differentiating EC cells in culture. This was evident from examination of RA-treated P19 cells in which the Wnt-1 promoter was used to express FLP. The temporal induction of Wnt-1 transcripts following RA-induced differentiation indicates that recombination occurred relatively quickly: FLP expression, recombination of the target transgene to reconstitute a functional lacZ gene, and subsequent βGal production occurred within twenty four hours. These results demonstrate that regulated rearrangement of a target sequence can be achieved.

The demonstration that Flp can excise DNA in mice and that the recombination product is heritable, suggests that Flp will be useful to study cell lineages. Considering this potential application, the initial test recombination substrate was designed to indicate and "remember" a recombination event by the irreversible gain of βGal activity (dependent only on constitutive promoter activity). Mice transgenic for this target should have the capability of marking cell lineages following introduction of Flp by crossing. Towards this end, mice transgenic for Wnt1::FLP have been generated; by crossing to an "optimal" target mouse, cells originating from the dorsal aspect of the developing central nervous system are predicted to be marked. Although all three FRTZ target lines analyzed here were competent for recombination, none of the recombined target alleles were sufficiently active to allow cell marking by XGal stain. The lack of βGal activity associated with the observed recombination most likely reflects a position effect on transgene transcription exerted by the genomic integration site since only one in four control FRTZ-product mouse lines expresses XGal. Such sensitivity to chromosomal context is also supported by the variation in transcript profiles observed when using the same hACTB regulatory sequences to direct FLP expression (two of five lines showed general expression). Importantly, by screening additional FRTZ target loci, a chromosomal integration site has been identified that can support lacZ expression following Flp-recombination.

These examples demonstrate that Flp can serve as a tool to alter a mammalian genome in vivo. By employing Flp and another recombinase (e.g., Cre and site-specific recombinases cited in U.S. Pat. No. 5,434,066), it should be possible to engineer multiple recombination reactions (multiple gene activation or inactivation events) in a transgenic non-human mammal.

While the present invention has been described in connection with what is presently considered to be practical and preferred embodiments, it is understood that the present invention is not to be limited or restricted to the disclosed embodiments but, on the contrary, is intended to cover various modifications and equivalent arrangements included within the spirit and scope of the appended claims.

Thus, it is to be understood that variations in the described invention will be obvious to those skilled in the art without departing from the novel aspects of the present invention and such variations are intended to come within the scope of the claims below. In particular, although the claimed invention is described in terms of the Flp recombinase, wild type Flp and the Flp-F70L mutant protein (SEQ ID NO:17), and the Flp-recognition sequence (e.g., FRT such as, for example, SEQ ID NOS:14 and 15), one skilled in the art would understand that functional equivalents of Flp recombinase and Flp-recognition sequences could be used in the context of the claimed invention and are intended to come within the scope of the claims below.

What is claimed is:

1. A transgenic mouse comprising a Flp recombinase transgene under control of a tissue-specific promoter integrated in a genome of the transgenic mouse, wherein the Flp recombinase transgene is expressed in a cell of the transgenic mouse at a level of recombinase activity sufficient to catalyze recombination between Flp-recognition sequences.

2. A transgenic mouse comprising a Flp recombinase transgene integrated into the genome of the transgenic mouse, wherein the Flp recombinase transgene is expressed from a tissue specific or a developmental stage specific promoter in at least one cell of the transgenic mouse at a level sufficient to catalyze recombination between two FLP-recognition sequences in direct repeat orientation in said cell, wherein said recombination is detected by activation of a gene expressed from a ubiquitous promoter, wherein said gene produces a detectable product only when in recombined form.

3. The transgenic mouse of claim 2, wherein said detectable product is a histochemical marker encoded by said gene selected from the group consisting of alkaline phosphatase, β-galactosidase, chloramphenicol acetyltransferase, luciferase, green fluorescent protein and β-glucuronidase.

4. The transgenic mouse of claim 2, wherein said detectable product is a transcript expressed from said gene in recombined form that is detectable by in situ hybridization.

5. The transgenic mouse of claim 2, wherein said detectable product is a peptide tag encoded by said gene that is detectable by binding to a cognate binder.

6. The transgenic mouse of claim 5, wherein said peptide tag and cognate binder pair are selected from the group consisting of avidin-biotin, GST-glutathione, polyHis-divalent metal, MBP-maltose, 9E10 Myc epitope-antibody, protein A/G-immunoglobulin and SV40 T antigen-antibody.

7. A method of mapping the developmental fate of a cell in vivo comprising:

(a) providing a transgenic mouse comprising a genome which contains a Flp recombinase transgene under control of a tissue-specific or developmental stage specific promoter and at least two FLP recognition sequences in direct repeat orientation;

(b) expressing the Flp recombinase transgene at a level sufficient to catalyze site-specific recombination between said FLP recognition sequences in at least one cell; and (c) detecting said recombination in said at least one cell by detecting activation of a gene expressed from a ubiquitous promoter, wherein said gene produces a detectable product only when in recombined form, and wherein said recombination is evidence of expression of said Flp recombinase transgene in said cell or a developmental precursor to said cell.

8. The method of claim 7, wherein said detectable product is a histochemical marker encoded by said gene selected from the group consisting of alkaline phosphatase, β-galactosidase, chloramphenicol acetyltransferase, luciferase, green fluorescent protein and β-glucuronidase.

9. The method of claim 7, wherein said detectable product is a transcript expressed from said gene in recombined form that is detectable by in situ hybridization.

10. The method of claim 7, wherein said detectable product is a peptide tag encoded by said gene that is detectable by binding to a cognate binder.

11. The method of claim 10, wherein said peptide tag and cognate binder pair are selected from the group consisting of avidin-biotin, GST-glutathione, polyHis-divalent metal, MBP-maltose, 9E10 Myc epitope-antibody, protein A/G-immunoglobulin and SV40 T antigen-antibody.

* * * * *

```
                          SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
           (A) LENGTH: 79 base pairs
           (B) TYPE: nucleic acid
           (C) STRANDEDNESS: single
           (D) TOPOLOGY: linear (xi) SEQUENCE DESCRIPTION: SEQ ID NO:1:

CCGGTGAAGT TCCTATTCCG AAGTTCCTAT TCTCTAGAAA GTATAGGAAC              50

TTCCCTAGGA GATCTTCGAA GGCTCGAGC                                    79

(2) INFORMATION FOR SEQ ID NO:2:

(i) SEQUENCE CHARACTERISTICS:
           (A) LENGTH: 59 base pairs
           (B) TYPE: nucleic acid
           (C) STRANDEDNESS: single
           (D) TOPOLOGY: linear (xi) SEQUENCE DESCRIPTION: SEQ ID NO:2:

TAGCTACGTA GAAGTTCCTA TTCCGAAGTT CCTATTCTCT AGAAAGTATA              50

GGAACTTCA                                                          59

(2) INFORMATION FOR SEQ ID NO:3:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (xi) SEQUENCE DESCRIPTION: SEQ ID NO:3:

CTAGGGAAGT TCCTATACTT TCTAGAGAAT AGGAACTTCG GAATAGGAAC              50

TTCA                                                               54

(2) INFORMATION FOR SEQ ID NO:4:
```

(i) SEQUENCE CHARACTERISTICS:
    (A) LENGTH: 84 base pairs
    (B) TYPE: nucleic acid
    (C) STRANDEDNESS: single
    (D) TOPOLOGY: linear (xi) SEQUENCE DESCRIPTION: SEQ ID NO:4:

CCGGTGAAGT TCCTATACTT TCTAGAGAAT AGGAACTTCG GAATAGGAAC          50

TTCTACGTAG CTAGCTCGAG CCTTCGAAGA TCTC                          84

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:5:

GTAAGGTACC GGTGAAGTTC CTA                                      23

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

TTCACCCACC GGTGAAGTTC CTA                                      23

(2) INFORMATION FOR SEQ ID NO:7:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (xi) SEQUENCE DESCRIPTION: SEQ ID NO:7:

GGTACCGAGC TCAGCCACCA TGACTGCTCC AAAGAAGAAG CGTAAGGTAC          50

CGGTGAAGTT CCTATTCCGA AGTTCCTATT CTCTAGAAAG TATAGGAACT         100

TCACCGGTGG GTGAAGACCA GAAACAGCAC CTCGAACTGA GCCGCGATAT         150

TGCCCAGCGT TTCAACGCGC TGTATGGCGA GATCGATCCC GTCGTTTTAC         200

AACGTCGTGA C                                                   211

(2) INFORMATION FOR SEQ ID NO:8:

(i) SEQUENCE CHARACTERISTICS:
        (A) LENGTH: 64 amino acids
        (B) TYPE: amino acid
        (C) STRANDEDNESS: single
        (D) TOPOLOGY: linear (xi) SEQUENCE DESCRIPTION: SEQ ID NO:8:

Met Thr Ala Pro Lys Lys Lys Arg Lys Val Pro Val Lys Phe Leu
1               5                   10                  15

Phe Arg Ser Ser Tyr Ser Leu Glu Ser Ile Gly Thr Ser Pro Val
                20                  25                  30

Gly Glu Asp Gln Lys Gln His Leu Glu Leu Ser Arg Asp Ile Ala
                35                  40                  45

```
Gln Arg Phe Asn Ala Leu Tyr Gly Glu Ile Asp Pro Val Val Leu
            50                  55                  60
Gln Arg Arg Asp
```

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:9:

```
Ala Pro Lys Lys Lys Arg Lys Val
1               5
```

(2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:10:

```
Lys Phe Leu Phe Arg Ser Ser Tyr Ser Leu Glu Ser Ile Gly Thr
1               5                   10                  15
Ser
```

(2) INFORMATION FOR SEQ ID NO:11:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:11:

```
Pro Val Gly Glu Asp Gln Lys Gln His Leu Glu Leu Ser Arg Asp
1               5                   10                  15
Ile Ala Gln Arg Phe Asn Ala Leu Tyr Gly Glu Ile
                20                  25
```

(2) INFORMATION FOR SEQ ID NO:12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:12:

```
GAAGTTCCTA TTC                                                        13
```

(2) INFORMATION FOR SEQ ID NO:13:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:13:

```
GAAGTTCCTA TAC                                                        13
```

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:14:

```
GAAGTTCCTA TTCTCTAGAA AGTATAGGAA CTTC                              34
```

(2) INFORMATION FOR SEQ ID NO:15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:15:

```
GAAGTTCCTA TTCCGAAGTT CCTATTCTCT AGAAAGTATA GGAACTTC               48
```

(2) INFORMATION FOR SEQ ID NO:16:

(i) SEQUENCE CHARACTERISTICS:
        (A) LENGTH: 1272 base pairs
        (B) TYPE: nucleic acid
        (C) STRANDEDNESS: single
        (D) TOPOLOGY: linear (xi) SEQUENCE DESCRIPTION: SEQ ID NO:16:

```
ATGCCACAAT TTGATATATT ATGTAAAACA CCACCTAAGG TGCTTGTTCG TCAGTTTGTG    60
GAAAGGTTTG AAAGACCTTC AGGTGAGAAA ATAGCATTAT GTGCTGCTGA ACTAACCTAT   120
TTATGTTGGA TGATTACACA TAACGGAACA GCAATCAAGA GAGCCACATT CATGAGCTAT   180
AATACTATCA TAAGCAATTC GCTGAGTTTG GATATTGTCA ACAAGTCACT GCAGTTTAAA   240
TACAAGACGC AAAAAGCAAC AATTCTGGAA GCCTCATTAA AGAAATTGAT TCCTGCTTGG   300
GAATTTACAA TTATTCCTTA CTATGGACAA AAACATCAAT CTGATATCAC TGATATTGTA   360
AGTAGTTTGC AATTACAGTT CGAATCATCG GAAGAAGCAG ATAAGGGAAA TAGCCACAGT   420
AAAAAAATGC TTAAAGCACT TCTAAGTGAG GGTGAAAGCA TCTGGGAGAT CACTGAGAAA   480
ATACTAAATT CGTTTGAGTA TACTTCGAGA TTTACAAAAA CAAAAACTTT ATACCAATTC   540
CTCTTCCTAG CTACTTTCAT CAATTGTGGA AGATTCAGCG ATATTAAGAA CGTTGATCCG   600
AAATCATTTA AATTAGTCCA AAATAAGTAT CTGGGAGTAA TAATCCAGTG TTTAGTGACA   660
GAGACAAAGA CAAGCGTTAG TAGGCACATA TACTTCTTTA GCGCAAGGGG TAGGATCGAT   720
CCACTTGTAT ATTTGGATGA ATTTTTGAGG AATTCTGAAC CAGTCCTAAA ACGAGTAAAT   780
AGGACCGGCA ATTCTTCAAG CAACAAGCAG GAATACCAAT TATTAAAAGA TAACTTAGTC   840
AGATCGTACA ACAAAGCTTT GAAGAAAAAT GCGCCTTATT CAATCTTTGC TATAAAAAAT   900
GGCCCAAAAT CTCACATTGG AAGACATTTG ATGACCTCAT TTCTTTCAAT GAAGGGCCTA   960
ACGGAGTTGA CTAATGTTGT GGGAAATTGG AGCGATAAGC GTGCTTCTGC CGTGGCCAGG  1020
ACAACGTATA CTCATCAGAT AACAGCAATA CCTGATCACT ACTTCGCACT AGTTTCTCGG  1080
TACTATGCAT ATGATCCAAT ATCAAAGGAA ATGATAGCAT TGAAGGATGA GACTAATCCA  1140
ATTGAGGAGT GGCAGCATAT AGAACAGCTA AAGGGTAGTG CTGAAGGAAG CATACGATAC  1200
CCCGCATGGA ATGGGATAAT ATCACAGGAG GTACTAGACT ACCTTTCATC CTACATAAAT  1260
AGACGCATAT AA                                                     1272
```

-continued (2) INFORMATION FOR SEQ ID NO:17:

(i) SEQUENCE CHARACTERISTICS:
       (A) LENGTH: 423 amino acids
       (B) TYPE: amino acid
       (C) STRANDEDNESS: single
       (D) TOPOLOGY: linear (xi) SEQUENCE DESCRIPTION: SEQ ID NO:17:

```
Met Pro Gln Phe Asp Ile Leu Cys Lys Thr Pro Pro Lys Val Leu
1               5                   10                  15

Val Arg Gln Phe Val Glu Arg Phe Glu Arg Pro Ser Gly Glu Lys
                20                  25                  30

Ile Ala Leu Cys Ala Ala Glu Leu Thr Tyr Leu Cys Trp Met Ile
                35                  40                  45

Thr His Asn Gly Thr Ala Ile Lys Arg Ala Thr Phe Met Ser Tyr
                50                  55                  60

Asn Thr Ile Ile Ser Asn Ser Leu Ser Leu Asp Ile Val Asn Lys
                65                  70                  75

Ser Leu Gln Phe Lys Tyr Lys Thr Gln Lys Ala Thr Ile Leu Glu
                80                  85                  90

Ala Ser Leu Lys Lys Leu Ile Pro Ala Trp Glu Phe Thr Ile Ile
                95                  100                 105

Pro Tyr Tyr Gly Gln Lys His Gln Ser Asp Ile Thr Asp Ile Val
                110                 115                 120

Ser Ser Leu Gln Leu Gln Phe Glu Ser Ser Glu Glu Ala Asp Lys
                125                 130                 135

Gly Asn Ser His Ser Lys Lys Met Leu Lys Ala Leu Leu Ser Glu
                140                 145                 150

Gly Glu Ser Ile Trp Glu Ile Thr Glu Lys Ile Leu Asn Ser Phe
                155                 160                 165

Glu Tyr Thr Ser Arg Phe Thr Lys Thr Lys Thr Leu Tyr Gln Phe
                170                 175                 180

Leu Phe Leu Ala Thr Phe Ile Asn Cys Gly Arg Phe Ser Asp Ile
                185                 190                 195

Lys Asn Val Asp Pro Lys Ser Phe Lys Leu Val Gln Asn Lys Tyr
                200                 205                 210

Leu Gly Val Ile Ile Gln Cys Leu Val Thr Glu Thr Lys Thr Ser
                215                 220                 225

Val Ser Arg His Ile Tyr Phe Phe Ser Ala Arg Gly Arg Ile Asp
                230                 235                 240

Pro Leu Val Tyr Leu Asp Glu Phe Leu Arg Asn Ser Glu Pro Val
                245                 250                 255

Leu Lys Arg Val Asn Arg Thr Gln Asn Ser Ser Ser Asn Lys Gln
                260                 265                 270

Glu Tyr Gln Leu Leu Lys Asp Asn Leu Val Arg Ser Tyr Asn Lys
                275                 280                 285

Ala Leu Lys Lys Asn Ala Pro Tyr Ser Ile Phe Ala Ile Lys Asn
                290                 295                 300

Gly Pro Lys Ser His Ile Gly Arg His Leu Met Thr Ser Phe Leu
                305                 310                 315

Ser Met Lys Gly Leu Thr Glu Leu Thr Asn Val Val Gly Asn Trp
                320                 325                 330

Ser Asp Lys Arg Ala Ser Ala Val Ala Arg Thr Thr Tyr Thr His
```

```
              335                 340                 345
Gln Ile Thr Ala Ile Pro Asp His Tyr Phe Ala Leu Val Ser Arg
              350                 355                 360
Tyr Tyr Ala Tyr Asp Pro Ile Ser Lys Glu Met Ile Ala Leu Lys
              365                 370                 375
Asp Glu Thr Asn Pro Ile Glu Glu Trp Gln His Ile Glu Gln Leu
              380                 385                 390
Lys Gly Ser Ala Glu Gly Ser Ile Arg Tyr Pro Ala Trp Asn Gly
              395                 400                 405
Ile Ile Ser Gln Glu Val Leu Asp Tyr Leu Ser Ser Tyr Ile Asn
              410                 415                 420

Arg Arg Ile
```

(2) INFORMATION FOR SEQ ID NO:18:

(i) SEQUENCE CHARACTERISTICS:
        (A) LENGTH: 1272 base pairs
        (B) TYPE: nucleic acid
        (C) STRANDEDNESS: single
        (D) TOPOLOGY: linear (xi) SEQUENCE DESCRIPTION: SEQ ID NO:18:

```
ATGCCACAAT TTGATATATT ATGTAAAACA CCACCTAAGG TGCTTGTTCG TCAGTTTGTG      60
GAAAGGTTTG AAAGACCTTC AGGTGAGAAA ATAGCATTAT GTGCTGCTGA ACTAACCTAT     120
TTATGTTGGA TGATTACACA TAACGGAACA GCAATCAAGA GAGCCACATT CATGAGCTAT     180
AATACTATCA TAAGCAATTC GCTGAGTTTC GATATTGTCA ACAAGTCACT GCAGTTTAAA     240
TACAAGACGC AAAAAGCAAC AATTCTGGAA GCCTCATTAA AGAAATTGAT TCCTGCTTGG     300
GAATTTACAA TTATTCCTTA CTATGGACAA AAACATCAAT CTGATATCAC TGATATTGTA     360
AGTAGTTTGC AATTACAGTT CGAATCATCG GAAGAAGCAG ATAAGGGAAA TAGCCACAGT     420
AAAAAAATGC TTAAAGCACT TCTAAGTGAG GGTGAAAGCA TCTGGGAGAT CACTGAGAAA     480
ATACTAAATT CGTTTGAGTA TACTTCGAGA TTTACAAAAA CAAAAACTTT ATACCAATTC     540
CTCTTCCTAG CTACTTTCAT CAATTGTGGA AGATTCAGCG ATATTAAGAA CGTTGATCCG     600
AAATCATTTA AATTAGTCCA AAATAAGTAT CTGGGAGTAA TAATCCAGTG TTTAGTGACA     660
GAGACAAAGA CAAGCGTTAG TAGGCACATA TACTTCTTTA GCGCAAGGGG TAGGATCGAT     720
CCACTTGTAT ATTTGGATGA ATTTTTGAGG AATTCTGAAC CAGTCCTAAA ACGAGTAAAT     780
AGGACCGGCA ATTCTTCAAG CAACAAGCAG GAATACCAAT TATTAAAAGA TAACTTAGTC     840
AGATCGTACA ACAAAGCTTT GAAGAAAAAT GCGCCTTATT CAATCTTTGC TATAAAAAAT     900
GGCCCAAAAT CTCACATTGG AAGACATTTG ATGACCTCAT TCTTTCAAT GAAGGGCCTA     960
ACGGAGTTGA CTAATGTTGT GGGAAATTGG AGCGATAAGC GTGCTTCTGC CGTGGCCAGG    1020
ACAACGTATA CTCATCAGAT AACAGCAATA CCTGATCACT ACTTCGCACT AGTTTCTCGG    1080
TACTATGCAT ATGATCCAAT ATCAAAGGAA ATGATAGCAT TGAAGGATGA GACTAATCCA    1140
ATTGAGGAGT GGCAGCATAT AGAACAGCTA AAGGGTAGTG CTGAAGGAAG CATACGATAC    1200
CCCGCATGGA ATGGGATAAT ATCACAGGAG GTACTAGACT ACCTTTCATC CTACATAAAT    1260
AGACGCATAT AA                                                        1272
```

(2) INFORMATION FOR SEQ ID NO:19:

(i) SEQUENCE CHARACTERISTICS:
        (A) LENGTH: 423 amino acids (B) TYPE: amino acid
(C) STRANDEDNESS: single
(D) TOPOLOGY: linear (xi) SEQUENCE DESCRIPTION: SEQ ID NO:19:

```
Met Pro Gln Phe Asp Ile Leu Cys Lys Thr Pro Pro Lys Val Leu
 1               5                  10                  15

Val Arg Gln Phe Val Glu Arg Phe Glu Arg Pro Ser Gly Glu Lys
                20                  25                  30

Ile Ala Leu Cys Ala Ala Glu Leu Thr Tyr Leu Cys Trp Met Ile
                35                  40                  45

Thr His Asn Gly Thr Ala Ile Lys Arg Ala Thr Phe Met Ser Tyr
                50                  55                  60

Asn Thr Ile Ile Ser Asn Ser Leu Ser Phe Asp Ile Val Asn Lys
                65                  70                  75

Ser Leu Gln Phe Lys Tyr Lys Thr Gln Lys Ala Thr Ile Leu Glu
                80                  85                  90

Ala Ser Leu Lys Lys Leu Ile Pro Ala Trp Glu Phe Thr Ile Ile
                95                 100                 105

Pro Tyr Tyr Gly Gln Lys His Gln Ser Asp Ile Thr Asp Ile Val
               110                 115                 120

Ser Ser Leu Gln Leu Gln Phe Glu Ser Ser Glu Glu Ala Asp Lys
               125                 130                 135

Gly Asn Ser His Ser Lys Lys Met Leu Lys Ala Leu Leu Ser Glu
               140                 145                 150

Gly Glu Ser Ile Trp Glu Ile Thr Glu Lys Ile Leu Asn Ser Phe
               155                 160                 165

Glu Tyr Thr Ser Arg Phe Thr Lys Thr Lys Thr Leu Tyr Gln Phe
               170                 175                 180

Leu Phe Leu Ala Thr Phe Ile Asn Cys Gly Arg Phe Ser Asp Ile
               185                 190                 195

Lys Asn Val Asp Pro Lys Ser Phe Lys Leu Val Gln Asn Lys Tyr
               200                 205                 210

Leu Gly Val Ile Ile Gln Cys Leu Val Thr Glu Thr Lys Thr Ser
               215                 220                 225

Val Ser Arg His Ile Tyr Phe Phe Ser Ala Arg Gly Arg Ile Asp
               230                 235                 240

Pro Leu Val Tyr Leu Asp Glu Phe Leu Arg Asn Ser Glu Pro Val
               245                 250                 255

Leu Lys Arg Val Asn Arg Thr Gln Asn Ser Ser Ser Asn Lys Gln
               260                 265                 270

Glu Tyr Gln Leu Leu Lys Asp Asn Leu Val Arg Ser Tyr Asn Lys
               275                 280                 285

Ala Leu Lys Lys Asn Ala Pro Tyr Ser Ile Phe Ala Ile Lys Asn
               290                 295                 300

Gly Pro Lys Ser His Ile Gly Arg His Leu Met Thr Ser Phe Leu
               305                 310                 315

Ser Met Lys Gly Leu Thr Glu Leu Thr Asn Val Val Gly Asn Trp
               320                 325                 330

Ser Asp Lys Arg Ala Ser Ala Val Ala Arg Thr Thr Tyr Thr His
               335                 340                 345

Gln Ile Thr Ala Ile Pro Asp His Tyr Phe Ala Leu Val Ser Arg
               350                 355                 360

Tyr Tyr Ala Tyr Asp Pro Ile Ser Lys Glu Met Ile Ala Leu Lys
```

|     |     |     |     |     |     |     |     |     |     |
| --- | --- | --- | --- | --- | --- | --- | --- | --- | --- |
| 365 | | | | 370 | | | | 375 | |
| Asp | Glu | Thr | Asn | Pro | Ile | Glu | Glu | Trp | Gln His Ile Glu Gln Leu |
| | | | | 380 | | | | 385 | 390 |
| Lys | Gly | Ser | Ala | Glu | Gly | Ser | Ile | Arg | Tyr Pro Ala Trp Asn Gly |
| | | | | 395 | | | | 400 | 405 |
| Ile | Ile | Ser | Gln | Glu | Val | Leu | Asp | Tyr | Leu Ser Ser Tyr Ile Asn |
| | | | | 410 | | | | 415 | 420 |
| Arg | Arg | Ile | | | | | | | |

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:20:

GGTCCAACTG CAGCCCAAGC TTCC                              24

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:21:

GTGGATCGAT CCTACCCCTT GCG                               23

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:22:

GACTGCTCCA AGAAGAAGC GTAAGG                          26

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:23:

GCTATTACGC CAGCTGGCGA AAGG                              24